(12) United States Patent
Vazquez et al.

(10) Patent No.: US 9,987,422 B2
(45) Date of Patent: Jun. 5, 2018

(54) FLUID INFUSION PATCH PUMP DEVICE WITH AUTOMATIC STARTUP FEATURE

(71) Applicant: MEDTRONIC MINIMED, INC., Northridge, CA (US)

(72) Inventors: Pablo Vazquez, Porter Valley, CA (US); Afshin Bazargan, Simi Valley, CA (US); Hubert K. Yeung, Porter Ranch, CA (US); Anthony C. Ng, Calabasas, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 420 days.

(21) Appl. No.: 14/662,119

(22) Filed: Mar. 18, 2015

(65) Prior Publication Data

US 2015/0265767 A1    Sep. 24, 2015

Related U.S. Application Data

(60) Provisional application No. 61/969,748, filed on Mar. 24, 2014.

(51) Int. Cl.
*A61M 5/172* (2006.01)
*A61M 5/162* (2006.01)
(Continued)

(52) U.S. Cl.
CPC ............ *A61M 5/162* (2013.01); *A61M 5/142* (2013.01); *A61M 5/158* (2013.01); *A61M 5/16804* (2013.01); *A61M 2005/1585* (2013.01)

(58) Field of Classification Search
CPC .......... A61M 2005/14208; A61M 2005/1585; A61M 5/14248; A61M 5/158;
(Continued)

(56) References Cited

U.S. PATENT DOCUMENTS 3,631,847 A    1/1972    Hobbs, II
4,212,738 A    7/1980    Henne
(Continued)

FOREIGN PATENT DOCUMENTS

DE    4329229    3/1995
EP    0319268    11/1988
(Continued)

OTHER PUBLICATIONS

PCT Search Report (PCT/US02/03299), dated Oct. 31, 2002, Medtronic Minimed, Inc.
(Continued)

*Primary Examiner* — Nathan R Price
*Assistant Examiner* — Gerald Landry, II
(74) *Attorney, Agent, or Firm* — Lorenz & Kopf, LLP

(57) ABSTRACT

A fluid infusion device and related operating methods are disclosed. The fluid infusion device has a housing, a fluid pump mechanism, a transcutaneous conduit assembly having a fluid conduit coupled to the pump mechanism, and an insertion mechanism for inserting the conduit into the body. An exemplary method begins by detecting a first installation of a fluid cartridge module in the housing, wherein the detecting occurs after the housing has been affixed to the body. In response to the detecting, the operating method automatically activates the insertion mechanism to insert the fluid conduit into the body.

17 Claims, 11 Drawing Sheets

(51) Int. Cl.
*A61M 5/142* (2006.01)
*A61M 5/168* (2006.01)
*A61M 5/158* (2006.01)

(58) Field of Classification Search
CPC .............. A61M 5/1723; A61M 5/142; A61M 2205/50; A61M 2005/14252; A61M 2005/14268; A61M 5/14244; A61M 2005/1581; A61M 2205/3592
USPC ...................................... 604/65–67, 131–155
See application file for complete search history.

(56) References Cited

U.S. PATENT DOCUMENTS

| | | |
|---|---|---|
| 4,270,532 A | 6/1981 | Franetzki et al. |
| 4,282,872 A | 8/1981 | Franetzki et al. |
| 4,373,527 A | 2/1983 | Fischell |
| 4,395,259 A | 7/1983 | Prestele et al. |
| 4,433,072 A | 2/1984 | Pusineri et al. |
| 4,443,218 A | 4/1984 | Decant, Jr. et al. |
| 4,494,950 A | 1/1985 | Fischell |
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Allen, III |
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,871,351 A | 10/1989 | Feingold |
| 4,898,578 A | 2/1990 | Rubalcaba, Jr. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,485,408 A | 1/1996 | Blomquist |
| 5,505,709 A | 4/1996 | Funderburk et al. |
| 5,497,772 A | 5/1996 | Schulman et al. |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Illiff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttila |
| 5,687,734 A | 11/1997 | Dempsey et al. |
| 5,704,366 A | 1/1998 | Tacklind et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach et al. |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,032,119 A | 2/2000 | Brown et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,183,412 B1 | 2/2001 | Benkowski et al. |
| 6,246,992 B1 | 6/2001 | Brown |
| 6,259,937 B1 | 7/2001 | Schulman et al. |
| 6,329,161 B1 | 12/2001 | Heller et al. |
| 6,408,330 B1 | 6/2002 | DeLaHuerga |
| 6,424,847 B1 | 7/2002 | Mastrototaro et al. |

(56) References Cited

U.S. PATENT DOCUMENTS

| | | | |
|---|---|---|---|
| 6,472,122 B1 | 10/2002 | Schulman et al. | |
| 6,484,045 B1 | 11/2002 | Holker et al. | |
| 6,484,046 B1 | 11/2002 | Say et al. | |
| 6,503,381 B1 | 1/2003 | Gotoh et al. | |
| 6,514,718 B2 | 2/2003 | Heller et al. | |
| 6,544,173 B2 | 4/2003 | West et al. | |
| 6,553,263 B1 | 4/2003 | Meadows et al. | |
| 6,554,798 B1 | 4/2003 | Mann et al. | |
| 6,558,320 B1 | 5/2003 | Causey, III et al. | |
| 6,558,351 B1 | 5/2003 | Steil et al. | |
| 6,560,741 B1 | 5/2003 | Gerety et al. | |
| 6,565,509 B1 | 5/2003 | Say et al. | |
| 6,579,690 B1 | 6/2003 | Bonnecaze et al. | |
| 6,591,125 B1 | 7/2003 | Buse et al. | |
| 6,592,745 B1 | 7/2003 | Feldman et al. | |
| 6,605,200 B1 | 8/2003 | Mao et al. | |
| 6,605,201 B1 | 8/2003 | Mao et al. | |
| 6,607,658 B1 | 8/2003 | Heller et al. | |
| 6,616,819 B1 | 9/2003 | Liamos et al. | |
| 6,618,934 B1 | 9/2003 | Feldman et al. | |
| 6,623,501 B2 | 9/2003 | Heller et al. | |
| 6,641,533 B2 | 11/2003 | Causey, III et al. | |
| 6,654,625 B1 | 11/2003 | Say et al. | |
| 6,659,980 B2 | 12/2003 | Moberg et al. | |
| 6,671,554 B2 | 12/2003 | Gibson et al. | |
| 6,676,816 B2 | 1/2004 | Mao et al. | |
| 6,689,265 B2 | 2/2004 | Heller et al. | |
| 6,728,576 B2 | 4/2004 | Thompson et al. | |
| 6,733,471 B1 | 5/2004 | Ericson et al. | |
| 6,746,582 B2 | 6/2004 | Heller et al. | |
| 6,747,556 B2 | 6/2004 | Medema et al. | |
| 6,749,740 B2 | 6/2004 | Liamos et al. | |
| 6,752,787 B1 | 6/2004 | Causey, III et al. | |
| 6,809,653 B1 | 10/2004 | Mann et al. | |
| 6,881,551 B2 | 4/2005 | Heller et al. | |
| 6,892,085 B2 | 5/2005 | McIvor et al. | |
| 6,893,545 B2 | 5/2005 | Gotoh et al. | |
| 6,895,263 B2 | 5/2005 | Shin et al. | |
| 6,916,159 B2 | 7/2005 | Rush et al. | |
| 6,932,584 B2 | 8/2005 | Gray et al. | |
| 6,932,894 B2 | 8/2005 | Mao et al. | |
| 6,942,518 B2 | 9/2005 | Liamos et al. | |
| 7,153,263 B2 | 12/2006 | Carter et al. | |
| 7,153,289 B2 * | 12/2006 | Vasko | A61M 5/142 128/904 |
| 7,396,330 B2 | 7/2008 | Banet et al. | |
| 7,749,186 B2 * | 7/2010 | Kohlbrenner | A61M 5/20 604/207 |
| 7,942,863 B2 * | 5/2011 | Kalpin | A61B 17/3403 604/288.02 |
| 7,946,984 B2 * | 5/2011 | Brister | A61B 5/0002 600/347 |
| 8,308,741 B2 * | 11/2012 | Hyde | A61B 10/0283 600/461 |
| 8,376,985 B2 * | 2/2013 | Pongpairochana | A61M 5/20 604/67 |
| 8,435,209 B2 * | 5/2013 | Hanson | A61M 5/1413 604/67 |
| 8,641,669 B2 * | 2/2014 | Renz | A61M 5/2066 604/135 |
| 8,690,855 B2 | 4/2014 | Alderete, Jr. et al. | |
| 8,905,972 B2 * | 12/2014 | Smith | A61M 5/14248 604/152 |
| 8,920,389 B2 * | 12/2014 | Kalpin | A61B 17/3403 604/288.01 |
| 9,610,405 B2 * | 4/2017 | Hanson | A61M 5/1413 |
| 2001/0044731 A1 | 11/2001 | Coffman et al. | |
| 2002/0013518 A1 | 1/2002 | West et al. | |
| 2002/0055857 A1 | 5/2002 | Mault et al. | |
| 2002/0082665 A1 | 6/2002 | Haller et al. | |
| 2002/0137997 A1 | 9/2002 | Mastrototaro et al. | |
| 2002/0161288 A1 | 10/2002 | Shin et al. | |
| 2003/0060765 A1 | 3/2003 | Campbell et al. | |
| 2003/0078560 A1 | 4/2003 | Miller et al. | |
| 2003/0088166 A1 | 5/2003 | Say et al. | |
| 2003/0144581 A1 | 7/2003 | Conn et al. | |
| 2003/0152823 A1 | 8/2003 | Heller | |
| 2003/0176183 A1 | 9/2003 | Drucker et al. | |
| 2003/0188427 A1 | 10/2003 | Say et al. | |
| 2003/0199744 A1 | 10/2003 | Buse et al. | |
| 2003/0208113 A1 | 11/2003 | Mault et al. | |
| 2003/0220552 A1 | 11/2003 | Reghabi et al. | |
| 2004/0061232 A1 | 4/2004 | Shah et al. | |
| 2004/0061234 A1 | 4/2004 | Shah et al. | |
| 2004/0064133 A1 | 4/2004 | Miller et al. | |
| 2004/0064156 A1 | 4/2004 | Shah et al. | |
| 2004/0073095 A1 | 4/2004 | Causey, III et al. | |
| 2004/0074785 A1 | 4/2004 | Holker et al. | |
| 2004/0093167 A1 | 5/2004 | Braig et al. | |
| 2004/0097796 A1 | 5/2004 | Berman et al. | |
| 2004/0102683 A1 | 5/2004 | Khanuja et al. | |
| 2004/0111017 A1 | 6/2004 | Say et al. | |
| 2004/0122353 A1 | 6/2004 | Shahmirian et al. | |
| 2004/0167465 A1 | 8/2004 | Mihai et al. | |
| 2004/0263354 A1 | 12/2004 | Mann et al. | |
| 2005/0038331 A1 | 2/2005 | Silaski et al. | |
| 2005/0038680 A1 | 2/2005 | McMahon et al. | |
| 2005/0059924 A1 | 3/2005 | Katz et al. | |
| 2005/0148938 A1 * | 7/2005 | Blomquist | A61M 5/14244 604/152 |
| 2005/0154271 A1 | 7/2005 | Rasdal et al. | |
| 2005/0192557 A1 | 9/2005 | Brauker et al. | |
| 2006/0122673 A1 | 6/2006 | Callister et al. | |
| 2006/0229694 A1 | 10/2006 | Schulman et al. | |
| 2006/0238333 A1 | 10/2006 | Welch et al. | |
| 2006/0293571 A1 | 12/2006 | Bao et al. | |
| 2007/0088521 A1 | 4/2007 | Shmueli et al. | |
| 2007/0135866 A1 | 6/2007 | Baker et al. | |
| 2008/0146996 A1 | 6/2008 | Smisson et al. | |
| 2008/0154503 A1 | 6/2008 | Wittenber et al. | |
| 2008/0255516 A1 * | 10/2008 | Yodfat | A61M 5/14248 604/151 |
| 2008/0306449 A1 * | 12/2008 | Kristensen | A61M 5/20 604/192 |
| 2009/0081951 A1 | 3/2009 | Erdmann et al. | |
| 2009/0082635 A1 | 3/2009 | Baldus et al. | |
| 2010/0106088 A1 * | 4/2010 | Yodfat | A61B 5/6849 604/112 |
| 2010/0121306 A1 * | 5/2010 | Yodfat | A61B 5/14532 604/500 |
| 2010/0152656 A1 | 6/2010 | Music | |
| 2010/0234797 A1 | 9/2010 | Gelfand et al. | |
| 2012/0184907 A1 | 7/2012 | Smith et al. | |
| 2012/0259282 A1 | 10/2012 | Alderete, Jr. et al. | |
| 2013/0160532 A1 | 6/2013 | Rivas et al. | |
| 2013/0177455 A1 | 7/2013 | Kamen et al. | |
| 2013/0249687 A1 * | 9/2013 | Kamen | G05D 7/0647 340/539.11 |
| 2014/0012229 A1 * | 1/2014 | Bokelman | A61M 5/20 604/506 |
| 2014/0058349 A1 | 2/2014 | Bazargan et al. | |
| 2014/0088556 A1 | 3/2014 | Makaveev et al. | |
| 2014/0094770 A1 | 4/2014 | Li et al. | |
| 2014/0142507 A1 * | 5/2014 | Armes | A61M 5/422 604/112 |
| 2014/0142508 A1 | 5/2014 | Dilanni et al. | |
| 2014/0276536 A1 * | 9/2014 | Estes | A61M 5/14244 604/500 |
| 2015/0202367 A1 * | 7/2015 | Plaschkes | A61M 5/24 604/506 |
| 2015/0290394 A1 * | 10/2015 | Murakami | A61M 5/20 604/518 |
| 2016/0026331 A1 * | 1/2016 | Chen | G06F 3/038 345/174 |

FOREIGN PATENT DOCUMENTS

| | | |
|---|---|---|
| EP | 0806738 | 11/1997 |
| EP | 0880936 | 12/1998 |
| EP | 1338295 | 8/2003 |
| EP | 1631036 A2 | 3/2006 |
| GB | 2218831 | 11/1989 |

(56) References Cited

FOREIGN PATENT DOCUMENTS

| WO | WO 96/20745 | 7/1996 |
|---|---|---|
| WO | WO 96/36389 | 11/1996 |
| WO | WO 96/37246 A1 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/058537 A2 | 8/2002 |
| WO | WO 03/001329 | 1/2003 |
| WO | WO 03/094090 | 11/2003 |
| WO | WO 2005/065538 A2 | 7/2005 |

OTHER PUBLICATIONS (Animas Corporation, 1999). Animas . . . bringing new life to insulin therapy.
Bode B W, et al. (1996). Reduction in Severe Hypoglycemia with Long-Term Continuous Subcutaneous Insulin Infusion in Type I Diabetes. Diabetes Care, vol. 19, No. 4, 324-327.
Boland E (1998). Teens Pumping it Up! Insulin Pump Therapy Guide for Adolescents. 2nd Edition.
Brackenridge B P (1992). Carbohydrate Gram Counting a Key to Accurate Mealtime Boluses in Intensive Diabetes Therapy. Practical Diabetology, vol. 11, No. 2, pp. 22-28.
Brackenridge, B P et al. (1995). Counting Carbohydrates How to Zero in on Good Control. MiniMed Technologies Inc.
Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.
Hirsch I B et al. (1990). Intensive Insulin Therapy for Treatment of Type I Diabetes. Diabetes Care, vol. 13, No. 12, pp. 1265-1283.
Kulkarni K et al. (1999). Carbohydrate Counting a Primer for Insulin Pump Users to Zero in on Good Control. MiniMed Inc.
Marcus A O et al. (1996). Insulin Pump Therapy Acceptable Alternative to Injection Therapy. Postgraduate Medicine, vol. 99, No. 3, pp. 125-142.
Reed J et al. (1996). Voice of the Diabetic, vol. 11, No. 3, pp. 1-38.
Skyler J S (1989). Continuous Subcutaneous Insulin Infusion [CSII] With External Devices: Current Status. Update in Drug Delivery Systems, Chapter 13, pp. 163-183. Futura Publishing Company.
Skyler J S et al. (1995). The Insulin Pump Therapy Book Insights from the Experts. MiniMed•Technologies.
Strowig S M (1993). Initiation and Management of Insulin Pump Therapy. The Diabetes Educator, vol. 19, No. 1, pp. 50-60.
Walsh J, et al. (1989). Pumping Insulin: The Art of Using an Insulin Pump. Published by MiniMed•Technologies.
(Intensive Diabetes Management, 1995). Insulin Infusion Pump Therapy. pp. 66-78.
Disetronic My Choice™ D-TRON™ Insulin Pump Reference Manual. (no date).
Disetronic H-TRON® plus Quick Start Manual. (no date).
Disetronic My Choice H-TRONplus Insulin Pump Reference Manual. (no date).
Disetronic H-TRON® plus Reference Manual. (no date).
(MiniMed, 1996). The MiniMed 506. 7 pages. Retrieved on Sep. 16, 2003 from the World Wide Web: http://web.archive.org/web/19961111054527/www.minimed.com/files/506_pic.htm.
(MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.
(MiniMed, 1996). FAQ: The Practical Things . . . pp. 1-4. Retrieved on Sep. 16, 2003 from the World Wide Web: http://web.archive.org/web/19961111054546/www.minimed.com/files/faq_pract.htm.
(MiniMed, 1997). Wanted: a Few Good Belt Clips! 1 page Retrieved on Sep. 16, 2003 from the World Wide Web: http://web.archive.org/web/19970124234559/www.minimed.com/files/mmn002.htm.
(MiniMed Technologies, 1994). MiniMed 506 Insulin Pump User's Guide.
(MiniMed Technologies, 1994). MiniMed™ Dosage Calculator Initial Meal Bolus Guidelines / MiniMed™ Dosage Calculator Initial Basal Rate Guidelines Percentage Method. 4 pages.
(MiniMed, 1996). MiniMer™ 507 Insulin Pump User's Guide.
(MiniMed, 1997). MiniMed™ 507 Insulin Pump User's Guide.
(MiniMed, 1998). MiniMed 507C Insulin Pump User's Guide.
(MiniMed International, 1998). MiniMed 507C Insulin Pump for those who appreciate the difference.
(MiniMed Inc., 1999). MiniMed 508 Flipchart Guide to Insulin Pump Therapy.
(MiniMed Inc., 1999). Insulin Pump Comparison / Pump Therapy Will Change Your Life.
(MiniMed, 2000). MiniMed® 508 User's Guide.
(MiniMed Inc., 2000). MiniMed® Now [I] Can Meal Bolus Calculator / MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump A Tradition of Excellence.
(Medtronic MiniMed, 2002). Medtronic MiniMed Meal Bolus Calculator and Correction Bolus Calculator. International Version.
Abel, P., et al., "Experience with an implantable glucose sensor as a prerequiste of an artificial beta cell," Biomed. Biochim. Acta 43 (1984) 5, pp. 577-584.
Bindra, Dilbir S., et al., "Design and in Vitro Studies of a Needle-Type Glucose Sensor for a Subcutaneous Monitoring," American Chemistry Society, 1991, 63, pp. 1692-1696.
Boguslavsky, Leonid, et al., "Applications of redox polymers in biosensors," Sold State Ionics 60, 1993, pp. 189-197.
Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.
Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analytica Chimica Acta, 249, 1991, pp. 43-54.
Gough, D. A., et al., "Two-Dimensional Enzyme Electrode Sensor for Glucose," Analytical Chemistry, vol. 57, No. 5, 1985, pp. 2351-2357.
Gregg, Brian A., et al., "Cross-Linked Redox Gels Containing Glucose Oxidase for Amperometric Biosensor Applications," Analytical Chemistry, 62, pp. 258-263.
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68, No. 18, Sep. 15, 1996, pp. 3173-3179.

(56) References Cited

OTHER PUBLICATIONS

Johnson, K.W., et al., "In vivo evaluation of an electroenzymatic glucose sensor implanted in subcutaneous tissue," Biosensors & Bioelectronics, 7, 1992, pp. 709-714.
Jönsson, G., et al., "An Electromechanical Sensor for Hydrogen Peroxide Based on Peroxidase Adsorbed on a Spectrographic Graphite Electrode," Electroanalysis, 1989, pp. 465-468.
Kanapieniene, J. J., et al., "Miniature Glucose Biosensor with Extended Linearity," Sensors and Actuators, B. 10, 1992, pp. 37-40.
Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52.
Koudelka, M., et al., "In-vivo Behaviour of Hypodermically Implanted Microfabricated Glucose Sensors," Biosensors & Bioelectronics 6, 1991, pp. 31-36.
Koudelka, M., et al., "Planar Amperometric Enzyme-Based Glucose Microelectrode," Sensors & Actuators, 18, 1989, pp. 157-165.
Mastrototaro, John J., et al., "An electroenzymatic glucose sensor fabricated on a flexible substrate," Sensors & Actuators, B. 5, 1991, pp. 139-144.
Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.
McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.
Monroe, D., "Novel Implantable Glucose Sensors," ACL, Dec. 1989, pp. 8-16.
Morff, Robert J., et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.
Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.
Nakamoto, S., et al., "A Lift-Off Method for Patterning Enzyme-Immobilized Membranes in Multi-Biosensors," Sensors and Actuators 13, 1988, pp. 165-172.
Nishida, Kenro, et al., "Clinical applications of teh wearable artifical endocrine pancreas with the newly designed needle-type glucose sensor," Elsevier Sciences B.V., 1994, pp. 353-358.
Nishida, Kenro, et al., "Development of a ferrocene-mediated needle-type glucose sensor covereed with newly designd biocompatible membrane, 2-methacryloyloxyethylphosphorylcholine -co-n-butyl nethacrylate," Medical Progress Through Technology, vol. 21, 1995, pp. 91-103.
Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.
Reach, G., "A Method for Evaluating in vivo the Functional Characteristics of Glucose Sensors," Biosensors 2, 1986, pp. 211-220.
Shaw, G. W., et al., "In vitro testing of a simply constructed, highly stable glucose sensor suitable for implantation in diabetic patients," Biosensors & Bioelectronics 6, 1991, pp. 401-406.
Shichiri, M., "A Needle-Type Glucose Sensor—A Valuable Tool Not Only for a Self-Blood Glucose Monitoring but for a Wearable Artifiical Pancreas," Life Support Systems Proceedings, XI Annual Meeting ESAO, Alpbach-Innsbruck, Austria, Sep. 1984, pp. 7-9.
Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.
Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.
Shichiri, Motoaki, et al., "Glycaemic Control in a Pacreatectomized Dogs with a Wearable Artificial Endocrine Pancreas," Diabetologia, vol. 24, 1983, pp. 179-184.
Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20.
Shichiri, M., et al., "Membrane design for extending the long-life of an implantable glucose sensor," Diab. Nutr. Metab., vol. 2, No. 4, 1989, pp. 309-313.
Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.
Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.
Shichiri, Motoaki, et al., "Wearable Artificial Endocrine Pancreas with Needle-Type Glucose Sensor," The Lancet, Nov. 20, 1982, pp. 1129-1131.
Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.
Shinkai, Seiji, "Molecular Recognitiion of Mono- and Di-saccharides by Phenylboronic Acids in Solvent Extraction and as a Monolayer," J. Chem. Soc., Chem. Commun., 1991, pp. 1039-1041.
Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.
Sternberg, Robert, et al., "Study and Development of Multilayer Needle-type Enzyme-based Glucose Microsensors," Biosensors, vol. 4, 1988, pp. 27-40.
Tamiya, E., et al., "Micro Glucose Sensors using Electron Mediators Immobilized on a Polypyrrole-Modified Electrode," Sensors and Actuators, vol. 18, 1989, pp. 297-307.
Tsukagoshi, Kazuhiko, et al., "Specific Complexation with Mono- and Disaccharides that can be Detected by Circular Dichroism," J. Org. Chem., vol. 56, 1991, pp. 4089-4091.
Urban, G., et al., "Miniaturized multi-enzyme biosensors integrated with pH sensors on flexible polymer carriers for in vivo applciations," Biosensors & Bioelectronics, vol. 7, 1992, pp. 733-739.
Ubran, G. et al., "Miniaturized thin-film biosensors using covalently immobilized glucose oxidase," Biosensors & Bioelectronics, vol. 6, 1991, pp. 555-562.
Velho, G., et al., "In vivo calibration of a subcutaneous glucose sensor for determination of subcutaneous glucose kinetics," Diab. Nutr. Metab., vol. 3, 1988, pp. 227-233.
Wang, Joseph, et al., "Needle-Type Dual Microsensor for the Simultaneous Monitoring of Glucose and Insulin," Analytical Chemistry, vol. 73, 2001, pp. 844-847.
Yamasaki, Yoshimitsu, et al., "Direct Measurement of Whole Blood Glucose by a Needle-Type Sensor," Clinics Chimica Acta, vol. 93, 1989, pp. 93-98.
Yokoyama, K., "Integrated Biosensor for Glucose and Galactose," Analytica Chimica Acta, vol. 218, 1989, pp. 137-142.

\* cited by examiner

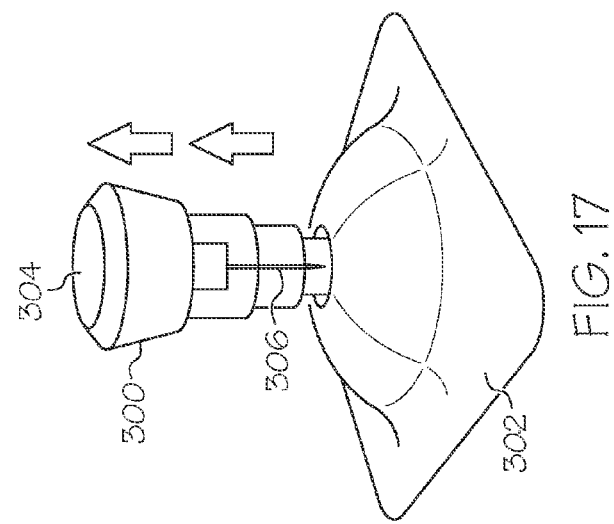
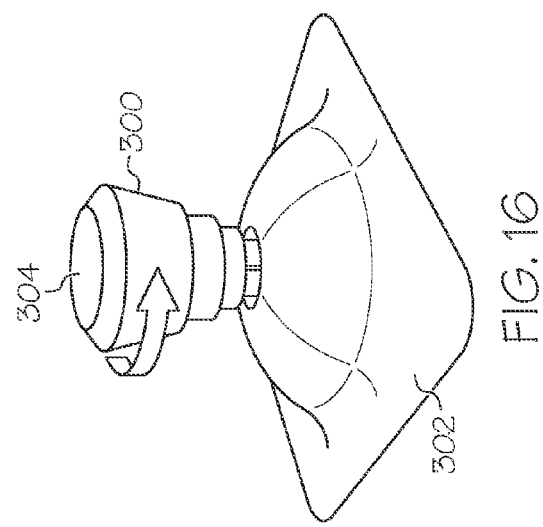
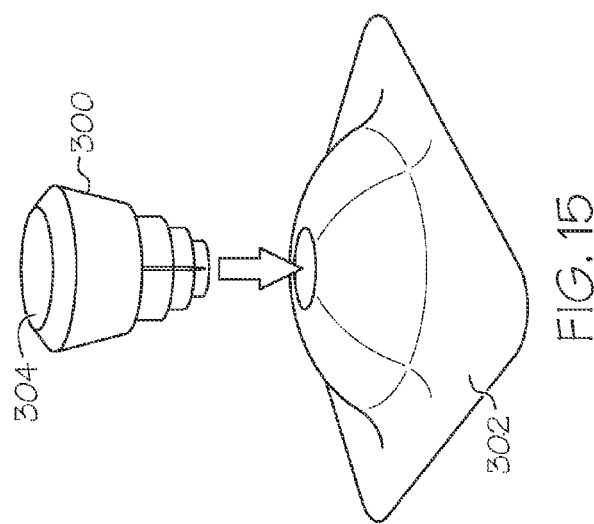

FLUID INFUSION PATCH PUMP DEVICE WITH AUTOMATIC STARTUP FEATURE

CROSS-REFERENCE TO RELATED APPLICATION

This application claims the benefit of U.S. provisional patent application No. 61/969,748, filed Mar. 24, 2014.

TECHNICAL FIELD

Embodiments of the subject matter described herein relate generally to fluid infusion devices of the type suitable for delivering a medication fluid to the body of a patient. More particularly, embodiments of the subject matter presented herein relate to features and operation of a simple fluid infusion patch pump device, which may be implemented as a prefilled device or as a device that is compatible with removable fluid cartridge modules.

BACKGROUND

Certain diseases or conditions may be treated, according to modern medical techniques, by delivering a medication fluid or other substance to the body of a patient, either in a continuous manner or at particular times or time intervals within an overall time period. For example, diabetes is commonly treated by delivering defined amounts of insulin to the patient at appropriate times. Some common modes of providing insulin therapy to a patient include delivery of insulin through manually operated syringes and insulin pens. Other modern systems employ programmable fluid infusion devices (e.g., insulin pumps) to deliver controlled amounts of insulin to a patient.

A fluid infusion device suitable for use as an insulin pump may be realized as an external device or an implantable device, which is surgically implanted into the body of the patient. External fluid infusion devices include devices designed for use in a generally stationary location (for example, in a hospital or clinic bedside environment), and devices configured for ambulatory or portable use (to be carried or worn by a patient). External fluid infusion devices may establish a fluid flow path from a fluid reservoir or cartridge to the patient via, for example, a suitable hollow tubing, needle, or other type of fluid conduit.

A fluid infusion device can be implemented as a simple and disposable product that is designed to be used for one to several days before being replaced. In this regard, fluid infusion patch pump devices are intended to be affixed to the skin of the patient such that medication fluid from a fluid reservoir or cartridge can be delivered directly from the patch pump device to the patient via a delivery needle or cannula of the patch pump device.

BRIEF SUMMARY

Various embodiments of a fluid infusion device and related operating methods are disclosed herein. In accordance with some embodiments, a fluid infusion device for delivering a medication fluid to a body includes a housing, a fluid pump mechanism enclosed within the housing, a subcutaneous conduit in fluid communication with the fluid pump mechanism, a drive motor enclosed within the housing and coupled to actuate the fluid pump mechanism, and a processor device operatively coupled to the drive motor. The housing receives removable fluid cartridge modules containing medication fluid. The processor device executes computer readable program instructions to perform a method that operates the fluid infusion device in a fluid delivery mode when a removable fluid cartridge module is in a seated position within the housing, and controls activation of the drive motor during the fluid delivery mode to cause the fluid pump mechanism to deliver a predetermined basal rate of the medication fluid to the body via the subcutaneous conduit. The method detects the occurrence of a cartridge removal event that is indicative of transition of the removable fluid cartridge module from the seated position to an unseated position. In response to the detecting, the fluid infusion device is operated in a suspend mode during which the drive motor is deactivated to disable the fluid pump mechanism and suspend delivery of the medication fluid to the body.

An exemplary embodiment of a method of operating a fluid infusion device is also presented herein. The fluid infusion device includes a housing, a fluid pump mechanism within the housing, and a drive motor within the housing and coupled to actuate the fluid pump mechanism. The method operates the fluid infusion device in a fluid delivery mode when a removable fluid cartridge module is installed in a seated position within the housing. The drive motor is activated during the delivery mode to cause the fluid pump mechanism to deliver a predetermined basal rate of medication fluid from the removable fluid cartridge module to a body via a subcutaneous conduit. The fluid infusion device detects a transition of the removable fluid cartridge module from the seated position to an unseated position. In response to the detecting, the fluid infusion device is operated in a suspend mode during which the drive motor is deactivated to disable the fluid pump mechanism and suspend delivery of the medication fluid to the body.

Also presented herein is a non-transitory computer readable storage media having program instructions that, when executed, perform a method of operating a fluid infusion device. An exemplary embodiment of the method involves operating the fluid infusion device in a fluid delivery mode when a removable fluid cartridge module is installed in a seated position within a housing of the fluid infusion device. A fluid pump mechanism of the fluid infusion device is activated during the fluid delivery mode to cause the fluid pump mechanism to deliver a predetermined basal rate of medication fluid from the removable fluid cartridge module to a body via a subcutaneous conduit. The method detects a transition of the removable fluid cartridge module from the seated position to an unseated position. In response to the detecting, the method operates the fluid infusion device in a suspend mode during which the fluid pump mechanism is disabled to suspend delivery of the medication fluid to the body.

Also presented herein is an exemplary embodiment of an insertion mechanism for actuating a transcutaneous conduit assembly having a fluid conduit and a needle. At least a portion of the needle is initially inside the fluid conduit. The insertion mechanism includes a first sliding block, a second sliding block, a torsion spring, and a living hinge. The first sliding block is coupled to the fluid conduit to move the fluid conduit in an insertion direction. The second sliding block is coupled to the needle to move the needle in the insertion direction and in a retraction direction. Movement of the second sliding block in the insertion direction pushes the first sliding block in the insertion direction. The living hinge is coupled between the torsion spring and the second sliding block, wherein rotation of the torsion spring during an insertion action actuates the living hinge to move the second sliding block in the insertion direction and, thereafter, in the retraction direction.

An exemplary embodiment of a fluid infusion device for delivering a medication fluid to a body is also presented herein. The fluid infusion device includes a housing, a fluid pump mechanism within the housing, an inlet conduit assembly in fluid communication with a fluid inlet of the fluid pump mechanism, wherein the inlet conduit assembly has structure compatible with a removable fluid cartridge module. The fluid infusion device also includes a transcutaneous conduit assembly in fluid communication with a fluid outlet of the fluid pump mechanism. The transcutaneous conduit assembly has a fluid conduit and a needle. The fluid infusion device also includes an insertion mechanism for actuating the transcutaneous conduit assembly. The insertion mechanism includes a first sliding block coupled to the fluid conduit to move the fluid conduit in an insertion direction, and a second sliding block coupled to the needle to move the needle in the insertion direction and in a retraction direction. Movement of the second sliding block in the insertion direction pushes the first sliding block in the insertion direction. The insertion mechanism also includes a torsion spring and a living hinge coupled between the torsion spring and the second sliding block. Rotation of the torsion spring during an insertion action actuates the living hinge to move the second sliding block in the insertion direction and, thereafter, in the retraction direction.

Another exemplary embodiment of a fluid infusion device for delivering a medication fluid to a body is presented herein. The fluid infusion device includes a housing that receives a removable fluid cartridge module, a transcutaneous conduit assembly having a fluid conduit and a needle, and an insertion mechanism for inserting the fluid conduit into the body. The insertion mechanism includes a first sliding block coupled to the fluid conduit to move the fluid conduit in an insertion direction. The insertion mechanism also includes a second sliding block coupled to the needle to move the needle in the insertion direction and in a retraction direction, wherein movement of the second sliding block in the insertion direction pushes the first sliding block in the insertion direction. The insertion mechanism also includes a torsion spring and a living hinge coupled between the torsion spring and the second sliding block, wherein rotation of the torsion spring during an insertion action actuates the living hinge to move the second sliding block in the insertion direction and, thereafter, in the retraction direction. The fluid infusion device also includes a lock mechanism to maintain the first sliding block and the second sliding block in an initial position and to maintain the torsion spring in a loaded state. The lock mechanism is automatically released to activate the insertion mechanism when the removable fluid cartridge module is installed in the housing.

Also presented herein is another embodiment of a fluid infusion device for delivering a medication fluid to a body. This embodiment of the fluid infusion device has a housing that receives a fluid cartridge module, a fluid pump mechanism within the housing, a transcutaneous conduit assembly having a fluid conduit in fluid communication with the fluid pump mechanism, an insertion mechanism for inserting the fluid conduit into the body, and a processor device operatively coupled to the drive motor. The processor device executes computer readable program instructions to initiate an automatic startup routine when the fluid cartridge module is initially installed in the housing. The insertion mechanism is automatically activated to insert the fluid conduit into the body when the fluid cartridge module is initially installed in the housing.

Another method of operating a fluid infusion device is presented herein. The fluid infusion device includes a housing, a fluid pump mechanism, a transcutaneous conduit assembly having a fluid conduit in fluid communication with the fluid pump mechanism, and an insertion mechanism for inserting the fluid conduit into the body. An exemplary embodiment of the method detects a first installation of a fluid cartridge module in the housing, wherein the detecting occurs after the housing has been affixed to the body. In response to the detecting, the method automatically activates the insertion mechanism to insert the fluid conduit into the body.

Another exemplary embodiment of a fluid infusion device for delivering a medication fluid to a body is presented herein. The fluid infusion device includes a housing that receives a fluid cartridge module, a fluid pump mechanism within the housing, a transcutaneous conduit assembly having a fluid conduit in fluid communication with the fluid pump mechanism, and an insertion mechanism for inserting the fluid conduit into the body. The insertion mechanism is automatically activated to insert the fluid conduit into the body when the fluid cartridge module is initially installed in the housing. After the insertion mechanism inserts the fluid conduit into the body, the fluid pump mechanism performs an automatic priming operation to prepare the fluid infusion device for delivery of the medication fluid.

Also presented herein is yet another embodiment of a fluid infusion device for delivering a medication fluid to a body. This embodiment of the fluid infusion device includes a housing that receives a fluid cartridge module containing the medication fluid, a fluid pump mechanism within the housing, the fluid pump mechanism having an inlet and an outlet, a first flow path in fluid communication with the inlet and at least partially defined by structure compatible with the fluid cartridge module, a second flow path in fluid communication with the outlet, the second flow path terminating at a subcutaneous conduit for the body, a drive motor enclosed within the housing and coupled to actuate the fluid pump mechanism, and a processor device operatively coupled to the drive motor. The processor device executes computer readable program instructions to initiate an automatic priming operation when the fluid cartridge module is initially installed in the housing.

Yet another method of operating a fluid infusion device is presented herein. The fluid infusion device has a housing, a fluid pump mechanism having an inlet and an outlet, a first flow path in fluid communication with the inlet and at least partially defined by structure compatible with fluid cartridge modules containing medication fluid, a second flow path in fluid communication with the outlet and terminating at a subcutaneous conduit for a body, and a drive motor coupled to actuate the fluid pump mechanism. An exemplary embodiment of the operating method detects a first installation of a fluid cartridge module in the housing, wherein the detecting occurs after the housing has been affixed to the body and after the subcutaneous conduit has been inserted into the body. In response to the detecting, the method initiates an automatic priming operation to prepare the fluid infusion device for delivery of the medication fluid to the body.

Also presented herein is a non-transitory computer readable storage media having program instructions that, when executed, perform a method of operating a fluid infusion device. An exemplary embodiment of the method detects a first installation of a fluid cartridge module in the fluid infusion device, wherein the detecting occurs after the fluid infusion device has been affixed to a body and after a subcutaneous conduit of the fluid infusion device has been inserted into the body. In response to the detecting, the program instructions initiate an automatic priming operation to prime the fluid infusion device with medication fluid obtained from the fluid cartridge module.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

FIGS. 15-17 are perspective views that illustrate operation of an external insertion mechanism that can be used with the fluid infusion device;

FIG. 18 is a block diagram representation of the system architecture of a fluid infusion device according to certain embodiments;

DETAILED DESCRIPTION

Figure 1:
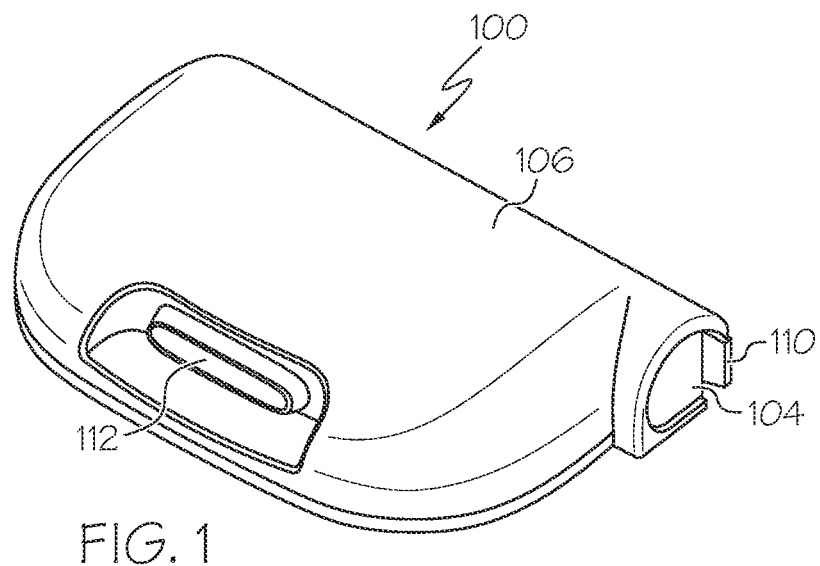
FIG. 1 is a top perspective view of an embodiment of a fluid infusion device implemented as a patch pump device.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Certain terminology may be used in the following description for the purpose of reference only, and thus are not intended to be limiting. For example, terms such as "upper", "lower", "above", and "below" could be used to refer to directions in the drawings to which reference is made. Terms such as "front", "back", "rear", "side", "outboard", and "inboard" could be used to describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

The following description relates to a fluid infusion device of the type used to treat a medical condition of a patient. The infusion device is used for infusing fluid (such as a medication) into the body of a user. The non-limiting examples described below relate to a medical device used to treat diabetes (more specifically, an insulin infusion device), although embodiments of the disclosed subject matter are not so limited. Accordingly, the infused medication fluid is insulin in certain embodiments. In alternative embodiments, however, many other fluids may be administered through infusion such as, but not limited to, disease treatments, drugs to treat pulmonary hypertension, iron chelation drugs, pain medications, anti-cancer treatments, medications, vitamins, hormones, or the like. For the sake of brevity, conventional features and characteristics related to infusion system operation, insulin pump operation, fluid reservoirs, and fluid conduits such as soft cannulas may not be described in detail here.

General Overview and System Architecture

Figure 2:
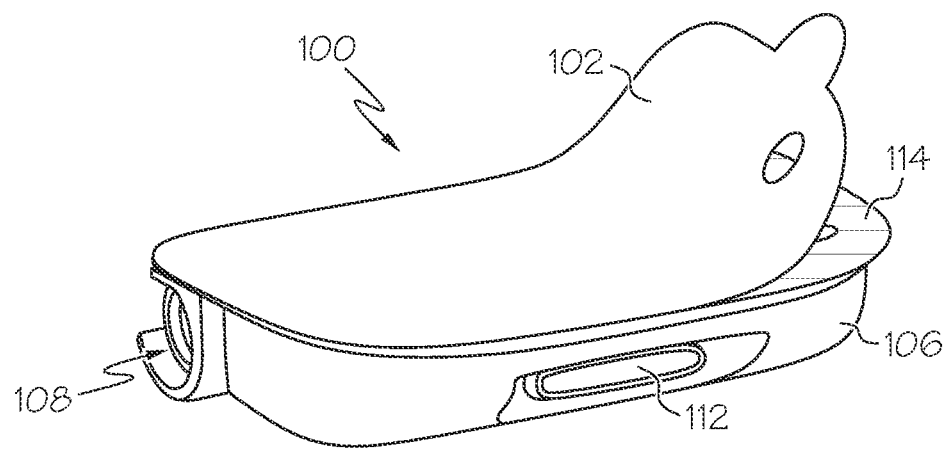
FIG. 2 is a bottom perspective view of the fluid infusion device, with an adhesive liner partially removed.
Figure 3:
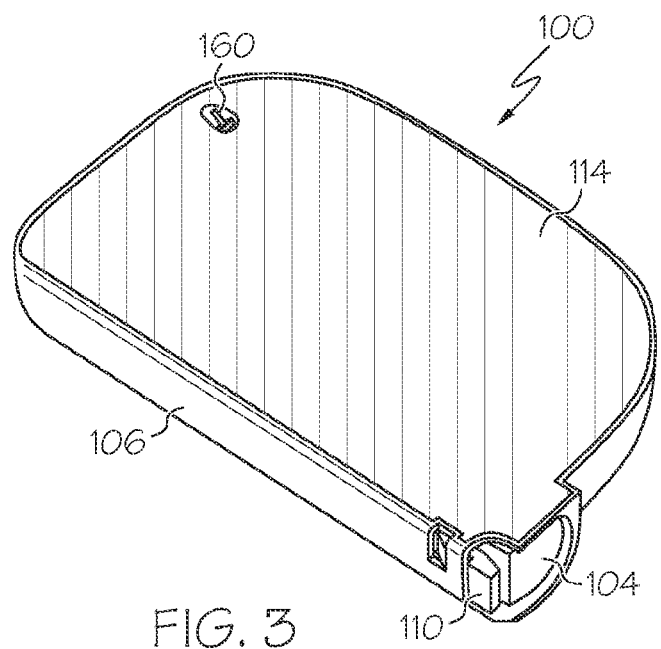
FIG. 3 is a bottom perspective view of the fluid infusion device, with the adhesive liner removed.
Figure 4:
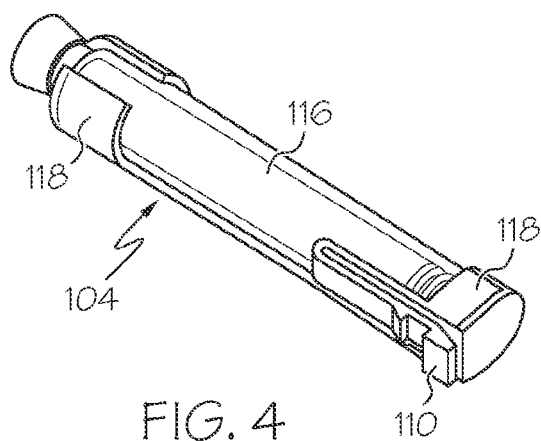
FIG. 4 is a perspective view of an embodiment of a removable fluid cartridge module that is compatible with the fluid infusion device.
Figure 5:
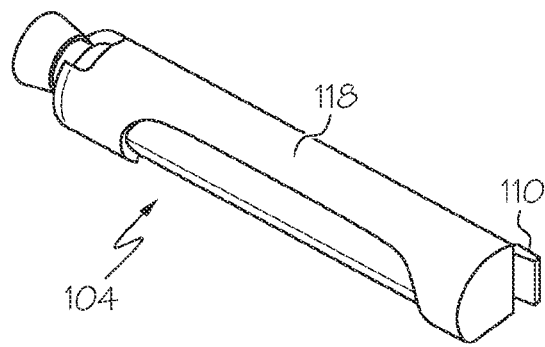
FIG. 5 is another perspective view of the removable fluid cartridge module.

FIG. 1 is a top perspective view of an embodiment of a fluid infusion device 100 implemented as a patch pump device, FIG. 2 is a bottom perspective view of the fluid infusion device 100 in a state where an adhesive liner 102 is partially removed, and FIG. 3 is a bottom perspective view of the fluid infusion device 100 with the adhesive liner 102 completely removed. FIG. 4 and FIG. 5 are perspective views of an exemplary embodiment of a removable fluid cartridge module 104 that is compatible with the fluid infusion device 100. FIG. 1 and FIG. 3 show the fluid infusion device 100 with the fluid cartridge module 104 installed and secured therein. In contrast, FIG. 2 shows the fluid infusion device 100 without the fluid cartridge module 104. The figures depict one possible configuration and form factor of the fluid infusion device 100. It should be appreciated that other designs and configurations can be utilized if so desired, and that the particular design aspects shown in the figures are not intended to limit or otherwise restrict the scope or application of the embodiments described herein.

The fluid infusion device 100 includes a housing 106 that serves as a shell for a variety of internal components. The housing 106 is suitably configured to receive, secure, and release the removable fluid cartridge module 104. In this regard, the fluid cartridge module 104 can be received in a suitably shaped, sized, and configured cavity 108 that is designed in accordance with certain physical characteristics of the fluid cartridge module 104. For example, the housing 106 can include structural features that mate with or otherwise engage structural features of the fluid cartridge module 104. The illustrated embodiment of the removable fluid cartridge module 104 includes a retention mechanism 110 that secures the fluid cartridge module 104 in the properly installed and seated position within the fluid infusion device 100. The retention mechanism 110 locks the fluid cartridge module 104 in place within the cavity 108 to maintain the necessary physical and fluid connections between the fluid cartridge module 104 and the fluid infusion device 100. The retention mechanism 110 can be physically manipulated to release the fluid cartridge module 104 from the housing 106 as needed (e.g., to replace one cartridge module with a different cartridge module, to remove the cartridge module when replacing an old fluid infusion device with a new fluid infusion device, or the like). In practice, the retention mechanism 110 can be realized as a latching feature, a locking feature, a tab, or the like. Regardless of the manner in which the retention mechanism 110 is implemented, it should be relatively easy and simple to intentionally remove the fluid cartridge module 104, while being difficult to unintentionally or accidentally remove.

The fluid infusion device 100 includes at least one user interface feature, which can be actuated by the patient as needed. The illustrated embodiment of the fluid infusion device 100 includes a button 112 that is physically actuated. The button 112 can be a multipurpose user interface if so desired to make it easier for the user to operate the fluid infusion device 100. In this regard, the button 112 can be used in connection with one or more of the following functions, without limitation: waking up the processor and/or electronics of the fluid infusion device 100; triggering an insertion mechanism for actuating a transcutaneous conduit assembly (e.g., inserting a cannula into the subcutaneous space, or similar region of the patient); configuring one or more settings of the fluid infusion device 100; initiating delivery of medication fluid; initiating a fluid priming operation; disabling alerts or alarms generated by the fluid infusion device 100; and the like. In lieu of the button 112, the fluid infusion device 100 can employ a slider mechanism, a pin, a lever, or the like.

The fluid infusion device 100 includes an adhesive element 114 (or an adhesive material) that can be used to affix the housing 106 to the body of the patient. The adhesive element 114 can be located on the bottom surface of the housing 106 (see FIG. 3) such that the housing 106 can be temporarily adhered to the skin of the patient. The adhesive element 114 can cover substantially all of the lower surface (as depicted), or it can only partially cover the lower surface if so desired. The adhesive element 114 may be, for example, a piece of double sided adhesive tape that is cut into the desired shape and size. The fluid infusion device 100 is manufactured with the adhesive liner 102 overlying the adhesive element 114. The adhesive liner 102 is peeled away to expose the sticky surface of the adhesive element 114 (see FIG. 2). The adhesive element 114 is chosen to be strong enough to maintain the fluid infusion device 100 in place for the desired period of time (which is typically between one to seven days) and strong enough to withstand typical use cases (e.g., showering, rainy days, physical exercise, etc.), while also being easy to remove without discomfort. Moreover, the adhesive element 114 is chosen to minimize the occurrence of skin irritation, allergic reactions, and the like.

Setup and operation of the fluid infusion device 100 is simple and straightforward for the patient. In this regard, the particular procedure for setup and initiation may vary from one embodiment to another, depending on the specific configuration, design, form factor, and/or optional settings of the fluid infusion device 100. In accordance with one high level method of operation, the fluid infusion device 100 is deployed in the following manner: (1) insert the fluid cartridge module 104 into the housing 106; (2) remove the adhesive liner 102; (3) affix the housing 106 to the body; and (4) insert the fluid delivery cannula into the body by pressing a button, pulling a tab, removing a safety pin, or otherwise activating an insertion mechanism to release a preloaded spring or equivalent actuation component. Thereafter, the fluid infusion device can be prepared for the delivery of the medication fluid as needed.

In accordance with a second high level method of operation, the fluid infusion device 100 is deployed in the following manner: (1) remove the adhesive liner 102; (2) affix the housing 106 to the body; and (3) insert the fluid cartridge module 104 into the housing 106. In accordance with this option, the action of installing the fluid cartridge module 104 into the housing 106 engages or moves a mechanical, electrical, magnetic, or other type of interface, which in turn releases a preloaded spring or equivalent actuation component to insert the fluid delivery cannula into the body. In other words, the introduction of the fluid cartridge module 104 automatically triggers a cannula insertion mechanism. Once the spring is released upon the first cartridge insertion, the fluid infusion device 100 is put into a different state such that subsequent installations of a fluid cartridge module will not trigger the insertion mechanism again. This option reduces the number of steps associated with the setup procedure, and makes it easier for the patient.

In accordance with a third high level method of operation, the fluid infusion device 100 is deployed in the following manner: (1) insert the fluid cartridge module 104 into the housing 106; (2) remove the adhesive liner 102; (3) affix the housing 106 to the body; and (4) press a bolus delivery button (or other user interface element), which in turn wakes up the fluid infusion device 100 and operates a motor that contacts a mechanical interface to release a preloaded spring or equivalent actuation component of a cannula insertion mechanism. Thereafter, the fluid infusion device can be prepared for the delivery of the medication fluid as needed.

In accordance with a fourth high level method of operation, the fluid infusion device 100 is deployed in the following manner: (1) insert the fluid cartridge module 104 into the housing 106; (2) remove the adhesive liner 102; (3) affix the housing 106 to the body; and (4) press a bolus delivery button (or other user interface element), which in turn wakes up the fluid infusion device 100 and activates a component to insert the fluid cannula into the body. For example, pressing the button can send a signal to a nickel titanium wire (or other type of memory wire) that fires a cannula insertion mechanism. Thereafter, the fluid infusion device can be prepared for the delivery of the medication fluid as needed. Other types of triggering/firing methodologies (other than those mentioned in the context of the third and fourth methods of operation) could also be utilized in an embodiment of the fluid infusion device 100.

In accordance with a fifth high level method of operation, the fluid infusion device 100 is deployed in the following manner: (1) insert the fluid cartridge module 104 into the housing 106; (2) remove the adhesive liner 102; (3) affix the housing 106 to the body; and (4) insert a steel or soft cannula to establish the fluid flow path to the body. In some embodiments, the patient inserts a steel cannula into the body by hand and, when the fluid infusion device 100 is removed from the skin, engages a pin or a button to retract the steel cannula (to prevent a sharps hazard). In alternative embodiments, any of the techniques described above for the other options can be leveraged to insert a rigid cannula into the body of the patient.

Figure 6:
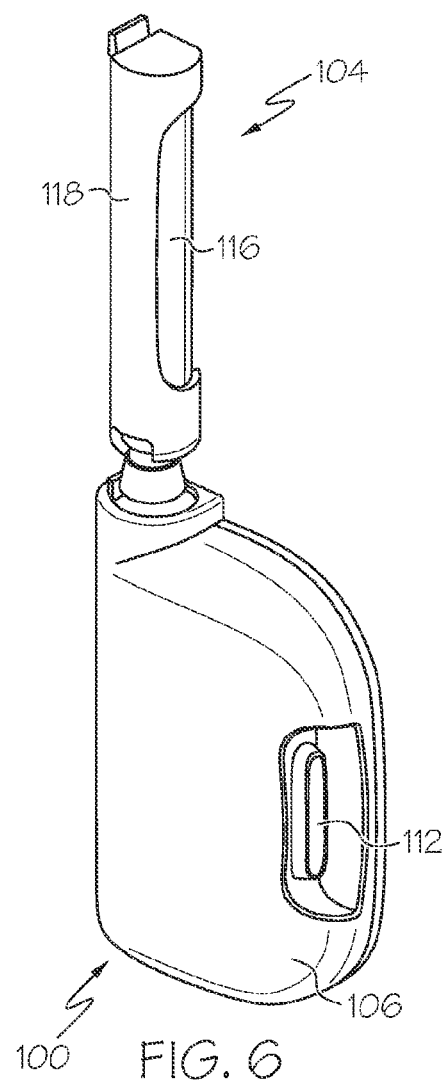
FIG. 6 is a perspective view that depicts the insertion of the removable fluid cartridge module into the fluid infusion device.

In certain embodiments, the fluid infusion device 100 is realized as a single-piece disposable component that is designed for continuous use over a designated period of time, such as three days. Although not always required, the fluid infusion device 100 can be designed to accommodate prefilled fluid cartridge modules 104, which may be provided by third party manufacturers in "off the shelf" volumes (e.g., 1.0 mL, 1.5 mL, 2.0 mL, or 3.0 mL of medication fluid). It should be appreciated that the fluid infusion device 100 can also be suitably configured and designed to accommodate user-filled fluid cartridge modules 104. Referring to FIG. 4 and FIG. 5, each removable fluid cartridge module 104 can be realized as a single-use disposable reservoir that is not designed or intended to be refilled. The illustrated embodiment of the fluid reservoir cartridge module 104 includes a glass or plastic reservoir 116 that is held in a carrier 118 or housing to facilitate insertion and removal of the reservoir 116. FIG. 6 is a perspective view that depicts the insertion of the removable fluid cartridge module 104 into the housing 106 of the fluid infusion device 100.

In certain embodiments, the carrier 118 can include or define: retention features; keying features to identify the medication type or concentration contained in the reservoir 116; detectable features that cooperate with sensor technology; etc. For example, when delivering insulin of U100 concentration, the carrier 118 can have a certain type of feature that is accepted by the housing 106 (such as a specific tongue and groove configuration). In contrast, a different U300 concentration medication can have a carrier 118 with a different type of slot that is accepted by a housing in a slightly different orientation. The identification of different medication type or concentration can be used by the fluid infusion device 100 to modify the fluid delivery algorithm and/or other operating characteristics of the fluid delivery system. In practice, there can be specific fluid infusion devices can be designed for specific concentrations of medication fluid. Accordingly, there can be a U100 device and a U300 device, each with corresponding keying features to prevent the use of incompatible fluid cartridges. Alternatively, there can be a single fluid infusion device where different cartridges can be accepted in different orientations to initiate adjustment of the fluid delivery algorithm. In yet other embodiments, the carrier 118 can have an embedded sensor element or detectable component, such as an RFID chip, a magnet, or the like, wherein the embedded element is used to identify the type or concentration of medication contained in the fluid cartridge module 104, which in turn results in an appropriate adjustment of the fluid delivery algorithm.

As mentioned above, an embodiment of the fluid infusion device 100 includes at least one user interface input element in the form of a physical button, a capacitive sensor, a force-sensitive resistor button, or the like. Certain embodiments can be outfitted with only one multifunction button that supports different operations, wherein the functionality of the single button can be controlled or regulated by the electronics onboard the fluid infusion device 100.

The fluid infusion device 100 can be offered as a product having only one product identifier (such as a stock keeping unit or SKU number). In such a scenario, the fluid infusion device 100 can be provided with software, processing logic, and/or a user interface element to enable a manufacturer, supplier, physician, caregiver, or other user to set the basal rate of fluid delivery, set a bolus amount corresponding to actuation of the bolus button, or both. Thus, a manufacturer of the fluid infusion device 100 need not design and offer different variations to accommodate different patients. Rather, the fluid infusion device 100 can be provided as a "generic" device that can be programmed or configured in a simple and straightforward manner.

In accordance with certain embodiments, the fluid infusion device 100 can be designed to interact with a coded key for purposes of setting or changing one or more fluid delivery parameters, operating characteristics, variables, or adjustments of the fluid infusion device 100. The key can be a physical key or it can be a physical feature of the fluid cartridge module 104. Alternatively (or additionally), the key may be a feature or element that can be electronically, magnetically, optically, or inductively read by the fluid infusion device 100, or read using other methodologies. For a physical implementation, the key can have a specific shape that corresponds to a particular bolus value, a specific basal rate, or the like. The key can interact with a component of the fluid infusion device 100 (e.g., a slot, a receptacle, or an electronics device that is mounted on a printed circuit board) to change the timing or other operating parameters of a drive motor to set the desired basal rate and bolus value corresponding to actuation of the button 112. The key can be installed on either the fluid infusion device 100 or on the fluid cartridge module 104.

In some embodiments, the keys are color coded to indicate different basal rates. For example, a green key might correspond to a basal rate of 2.0 Units/hr, a red key might correspond to a basal rate of 5.0 Units/hr, and the like. In some embodiments, different keys can be used to distinguish different types of medication fluid. For example, different keys might be used to identify different insulin concentration types (such as U100, U200, U300, etc.). In some embodiments, a coded key can also be used to trigger the cannula insertion mechanism of the fluid infusion device 100. Thus, the act of installing a compatible key into the fluid infusion device 100 (after the device has been affixed to the body) can activate the cannula insertion mechanism during the setup procedure described above, while also setting the desired therapy rate and/or bolus value. Moreover, installation of a coded key can automatically initiate other features or functions of the fluid infusion device 100, such as any of the cartridge-triggered functions described in more detail below.

Figure 7:
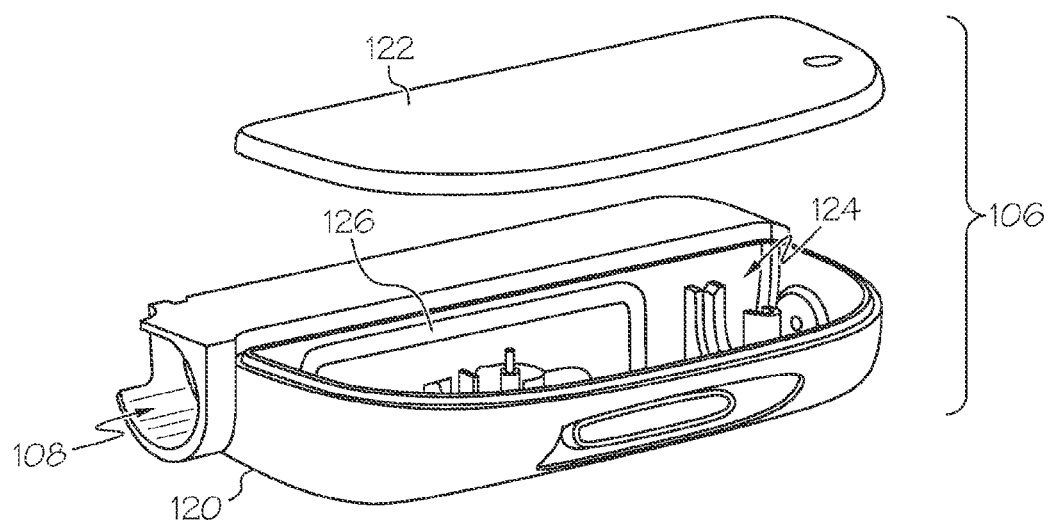
FIG. 7 is an exploded perspective view of the housing of the fluid infusion device.

As mentioned above, the housing 106 of the fluid infusion device 100 receives the removable fluid cartridge module 104 containing the desired medication fluid. The housing 106 also serves to contain the variety of components and elements that cooperate to support the functionality of the fluid infusion device 100. FIG. 7 is an exploded perspective view of the housing 106, which includes a primary housing shell 120 and a lid 122. The primary housing shell 120 generally includes two compartments defined therein: the cavity 108 for the removable fluid cartridge module 104; and a component cavity 124 for most of the remaining components of the fluid infusion device 100. In alternative embodiments, the lid 122 can be redesigned to provide some or all of the physical features and functionality described and shown herein with reference to the primary housing shell 120. For example, although the illustrated embodiment of the primary housing shell 120 includes retaining features for the removable fluid cartridge module 104, such retaining features could instead be provided in the lid 122.

The lid 122 can be affixed to the component cavity 124 to protect and seal the various components inside the component cavity 124. In some embodiments, the primary housing shell 120 includes one or more electrically conductive traces 126 printed thereon (e.g., metalized surfaces fabricated on molded plastic). The conductive traces 126 are desirable to reduce parts count, to make assembly easier, to improve reliability, and to reduce the size of the fluid infusion device 100. Of course, other embodiments may utilize physical connectors, conductive tapes, conductive rubber materials, wires, and the like. Furthermore, other electrical connections and couplings can be established with specifically configured parts or components. For example, the fluid infusion device 100 may include thin metal strips between a component, wherein the component is encased in a thin plastic housing, and the metal strips are soldered to an electric circuit board.

Figure 9:
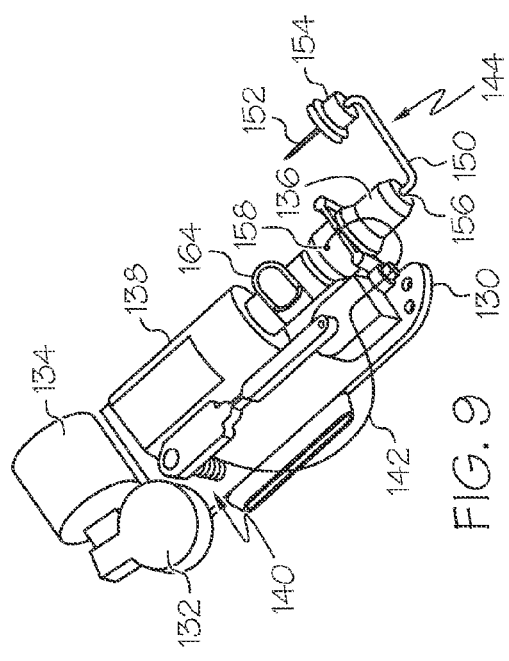
FIG. 9 is a perspective view of internal components of the fluid infusion device as assembled.
Figure 10:
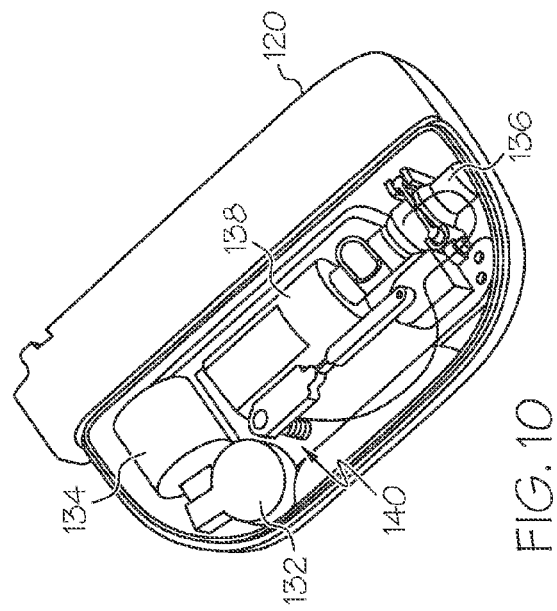
FIG. 10 is a perspective view of the internal components of the fluid infusion device as situated in the primary housing shell.
Figure 8:
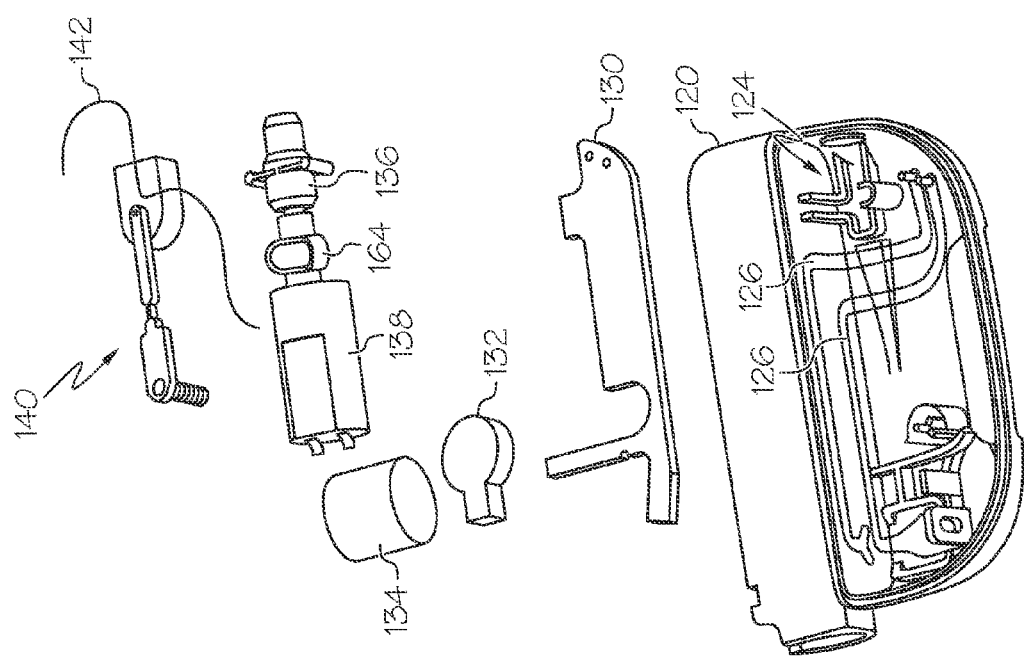
FIG. 8 is an exploded perspective view of the primary housing shell and internal components of the fluid infusion device.

FIG. 8 is an exploded perspective view of the primary housing shell 120 and internal components of the fluid infusion device 100, FIG. 9 is a perspective view of the internal components as assembled, and FIG. 10 is a perspective view of the internal components as situated in the primary housing shell 120. An embodiment of the fluid infusion device 100 may include additional features, components, devices, and elements that are not depicted in the figures.

Referring to FIG. 8, embodiments of the fluid infusion device 100 may include, without limitation: a printed circuit board 130; a vibration motor 132 or other haptic feedback element; a battery 134 or other energy source; a fluid pump mechanism 136; a drive motor 138 coupled to actuate the fluid pump mechanism 136, or other devices, components, or means to actuate the fluid pump mechanism 136, such as a solenoid, a nickel-titanium memory wire, or the like; an insertion mechanism 140 for actuating a transcutaneous conduit assembly; and an outlet fluid conduit 142. The internal components may also include an inlet conduit assembly 144 (shown in FIG. 9). The internal components are designed to facilitate quick and easy drop-in, press-fit, or snap-fit assembly into the component cavity 124. To further simplify the assembly of the fluid infusion device 100, the primary housing shell 120 may include living hinges that are molded into the plastic material that forms the primary housing shell 120. The living hinges can have conductive traces 126 printed thereon to establish press-fit electrical connections with components such as the battery 134. The vibration motor 132 can have electrical contacts on its bottom surface, such that the electrical contacts establish electrical connection with the underlying printed circuit board 130 when the vibration motor 132 is secured in position. Similarly, the drive motor 138 may have contacts that establish electrical connections when the drive motor 138 is snapped into place within the component cavity 124.

The mechanical packaging and assembly of the components of the fluid infusion device 100 are intended to keep the printed circuit board 130 centralized, so that sensors can be edge-mounted on the printed circuit board 130. This allows the sensors to interact with the drive motor 138, the fluid pump mechanism 136, and/or the button 112 in a direct manner. In other words, edge-mounting can further reduce the amount of electrical connectors, conductors, and traces needed to assemble the fluid infusion device 100.

The printed circuit board 130 can be a flexible substrate, a combination of a rigid substrate and a flexible substrate, or the like. The printed circuit board 130 includes various electronic components, devices, and connections that cooperate to support the functions of the fluid infusion device 100. These components are enclosed within the housing 106 for protection, water resistance, and the like. The printed circuit board 130 may include or cooperate with any of the following, without limitation: switches; adjustment or trim elements such as a potentiometer; a processor device; memory; or the like. The vibration motor 132 can be used to generate confirmation or alert signals as needed. Alternatively or additionally, the fluid infusion device 100 can include an audio transducer, an indicator light, a display element, or other components to provide feedback to the user. The battery 134 can be a single use element that can be discarded with the fluid infusion device. The battery 134 provides the required voltage and current to operate the fluid infusion device 100.

The fluid pump mechanism 136 can be realized as a rotationally actuated micro pump that delivers a calibrated amount of medication fluid with each delivery cycle. In this regard, the fluid pump mechanism 136 includes a stator and a rotor; the rotor is actuated in a controlled manner by the drive motor 138. The fluid pump mechanism 136 functions by rotating the rotor up and off a ramp or a slope that is integrated with the stator. Such rotation results in axial translation of the rotor relative to the stator. In turn, the translational movement results in the opening and closing of a series of valves that are internal to the fluid pump mechanism 136 for purposes of drawing in the medication fluid from the fluid cartridge module 104. A biasing force (e.g., a spring force) forces the rotor into the stator at the end of the ramp, which expels the fluid through the outlet of the fluid pump mechanism 136. In certain embodiments, the fluid pump mechanism 136 leverages the pump technology offered by Sensile Medical, although other types of pump technologies can also be utilized.

In accordance with certain embodiments, the biasing force that urges the rotor into the stator is provided by a molded plastic part that serves as both the spring element and a coupling component (to mechanically couple the drive motor 138 to the rotor). This spring coupler 164 is shown in FIG. 8 and FIG. 9. The spring coupler 164 eliminates the need for a separate coupling element, which reduces parts count, reduces product cost, and simplifies manufacturing and assembly of the fluid infusion device 100. The spring coupler 164 can be a physically distinct component that is mechanically attached between the drive motor 138 and the rotor of the fluid pump mechanism 136. In alternative embodiments, the spring coupler 164 can be integrally fabricated with the rotor.

The drive motor 138 can be a direct current (DC) motor, a brushless DC motor, a stepper motor, or the like. It should be appreciated that other drive methodologies could be used instead of the drive motor 138, such as a nickel titanium memory wire and a ratcheting mechanism to create rotational motion to drive the fluid pump mechanism 136.

Thus, a full rotation of the rotor results in the delivery of a known amount of medication fluid. After the fluid flow path of the fluid infusion device 100 has been primed, each rotation of the rotor draws a measured volume of medication fluid from the fluid cartridge module and expels the same amount of medication fluid from the cannula situated in the patient.

Referring to FIG. 9, the inlet conduit assembly 144 includes structure that is compatible with the removable fluid cartridge module 104. For example, the inlet conduit assembly 144 includes a fluid conduit 150 that terminates at a hollow reservoir needle 152. The hollow reservoir needle 152 enters the reservoir of the fluid cartridge module 104 (via a septum) when the fluid cartridge module 104 is installed in the fluid infusion device 100. The fluid infusion device 100 also includes a sealing element 154, which may be coupled to the inlet conduit assembly 144 (alternatively, the sealing element 154 can be an integral part of the inlet conduit assembly 144). The sealing element 154 can be a compressible and resilient component that creates a fluid seal for the inlet conduit assembly 144 when the fluid cartridge module 104 is removed from the housing 106 of the fluid infusion device 100. More specifically, the sealing element 154 is compressed when the fluid cartridge module 104 is installed, thus exposing the hollow reservoir needle 152 (as depicted in FIG. 9). The sealing element 154 extends to cover the end of the hollow reservoir needle 152 when the fluid cartridge module 104 is removed, which inhibits the ingress of contaminants, fluid, and air into the inlet conduit assembly 144, and which inhibits leakage of medication fluid from the fluid flow path of the fluid infusion device 100.

Moreover, the inlet conduit assembly 144 is in fluid communication with a fluid inlet 156 of the fluid pump mechanism 136. The fluid inlet 156 accommodates and receives an end of the fluid conduit 150, as shown in FIG. 9. This arrangement allows the fluid pump mechanism 136 to draw the medication fluid in from the fluid cartridge module 104, via the inlet conduit assembly 144. The fluid pump mechanism 136 expels the medication fluid from a fluid outlet 158, which is in fluid communication with the outlet fluid conduit 142.

The outlet fluid conduit 142 may be realized as part of a transcutaneous conduit assembly of the fluid infusion device 100, wherein the transcutaneous conduit assembly also includes a subcutaneous conduit (e.g., a soft cannula) that is inserted and positioned within the body of the patient. The subcutaneous conduit is hidden from view in FIG. 9, although FIG. 3 shows the distal end of the subcutaneous conduit 160 protruding from the housing 106 of the fluid infusion device 100. The transcutaneous conduit assembly is in fluid communication with the fluid outlet 158 of the fluid pump mechanism 136. More specifically, in accordance with the illustrated embodiment, the outlet fluid conduit 142 is implemented as a flexible hollow needle having its proximal end fluidly coupled to the fluid outlet 158. The distal end of the flexible hollow needle is sharp to accommodate the insertion of the subcutaneous conduit 160 into the body of the patient during an insertion operation. The distal end of the flexible hollow needle is hidden from view in FIG. 9. The proximal end of the subcutaneous conduit 160 is fluidly coupled to the flexible hollow needle such that at least a portion of the needle is initially inside the subcutaneous conduit 160 (i.e., the subcutaneous conduit 160 is carried by the flexible hollow needle before and during an insertion operation). Accordingly, the subcutaneous conduit 160 is in fluid communication with the fluid pump mechanism 136 such that the medication fluid can be delivered to the body of the patient via the outlet fluid conduit 142 and the subcutaneous conduit 160. The manner in which the subcutaneous conduit 160 is inserted into the body of the patient is described in more detail below with reference to FIGS. 11-17 and FIGS. 19-24.

The fluid infusion device 100 includes a flow path that accommodates the delivery of the medication fluid from the fluid cartridge module 104 to a subcutaneous site in the body of the patient. A first fluid flow path is at least partially defined by the inlet conduit assembly 144, which resides between the fluid cartridge module 104 and the fluid pump mechanism 136. The first fluid flow path may be considered to be the inlet flow path of the fluid pump mechanism 136. A second flow path (which may be considered to be the outlet flow path of the fluid pump mechanism 136) is defined by the outlet fluid conduit 142 and the subcutaneous conduit 160. In this regard, the second flow path terminates at the distal end of the subcutaneous conduit 160. The overall flow path of the fluid infusion device 100, therefore, includes the first fluid flow path, the fluid pump mechanism 136, and the second fluid flow path. It should be appreciated that the fluid flow path through the fluid infusion device 100 can be established using any number of rigid needles (bent or straight), soft tubing, flexible steel tubing, or the like. The particular embodiment described herein is merely one possible arrangement.

The fluid infusion device 100 can be outfitted with a suitably configured insertion mechanism for actuating the transcutaneous conduit assembly to insert the subcutaneous conduit 160 into the body of the patient. In accordance with one methodology, the insertion mechanism of the fluid infusion device 100 employs a linear two-spring architecture. FIGS. 11-14 are simplified diagrams that show the operation of a linear two-spring insertion mechanism 200 suitable for use with the fluid infusion device 100. The insertion mechanism 200 includes a first element 202 coupled to a needle 204. The first element 202 is preloaded by a spring 206; the first element 202 is held in place by a first stopper pin 208. The insertion mechanism 200 also includes a second element 210. The second element is preloaded by a spring 212; the second element is held in place by a second stopper pin 214. The stopper pins 208, 214 can be realized as buttons, pull tabs, removable pins, or the like.

Figure 13:
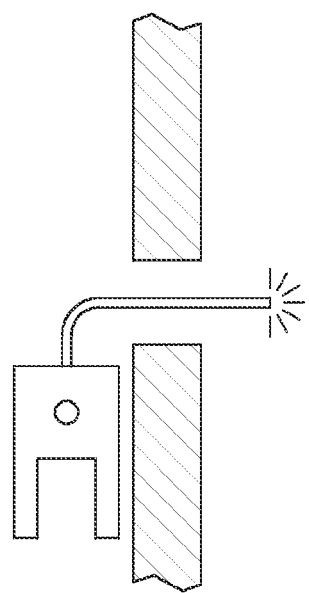
FIG. 13 is a diagram that shows a side view of a portion of the conduit insertion mechanism in a deployed state.
Figure 14:
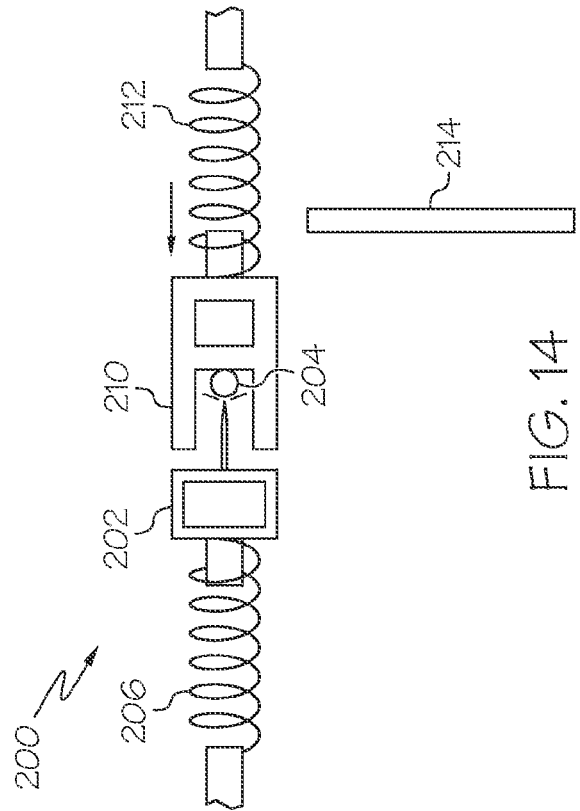
FIG. 14 is a diagram of the conduit insertion mechanism shown in a retracted state.
Figure 11:
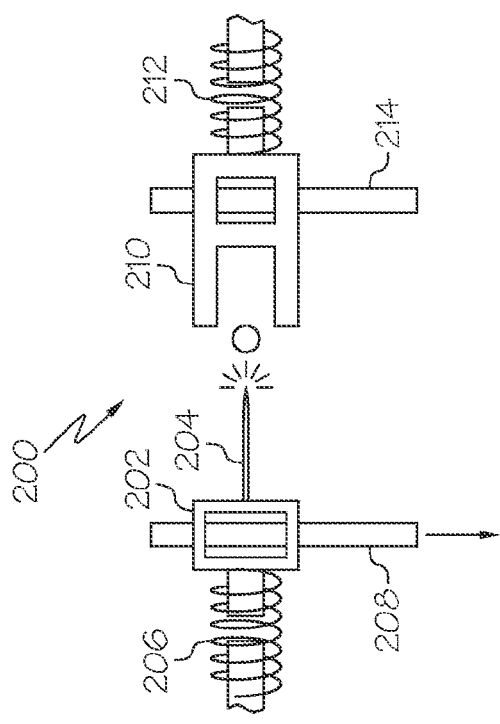
FIG. 11 is a diagram of a conduit insertion mechanism suitable for use with the fluid infusion device, where the insertion mechanism is in an initial state.
Figure 12:
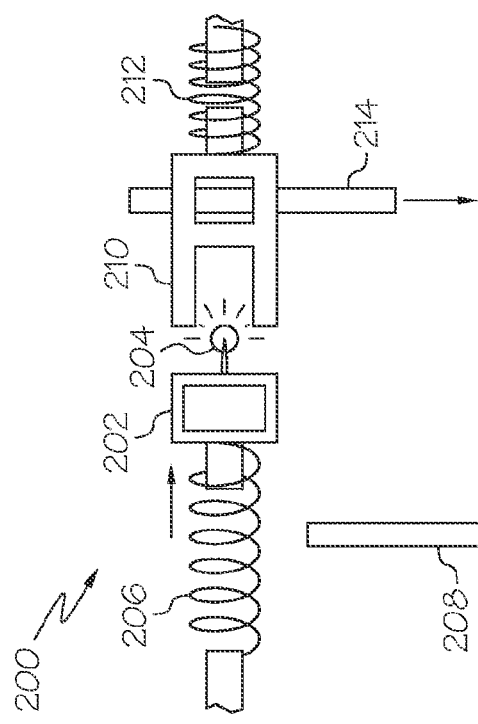
FIG. 12 is a diagram of the conduit insertion mechanism shown in a deployed state.
Figure 1B:
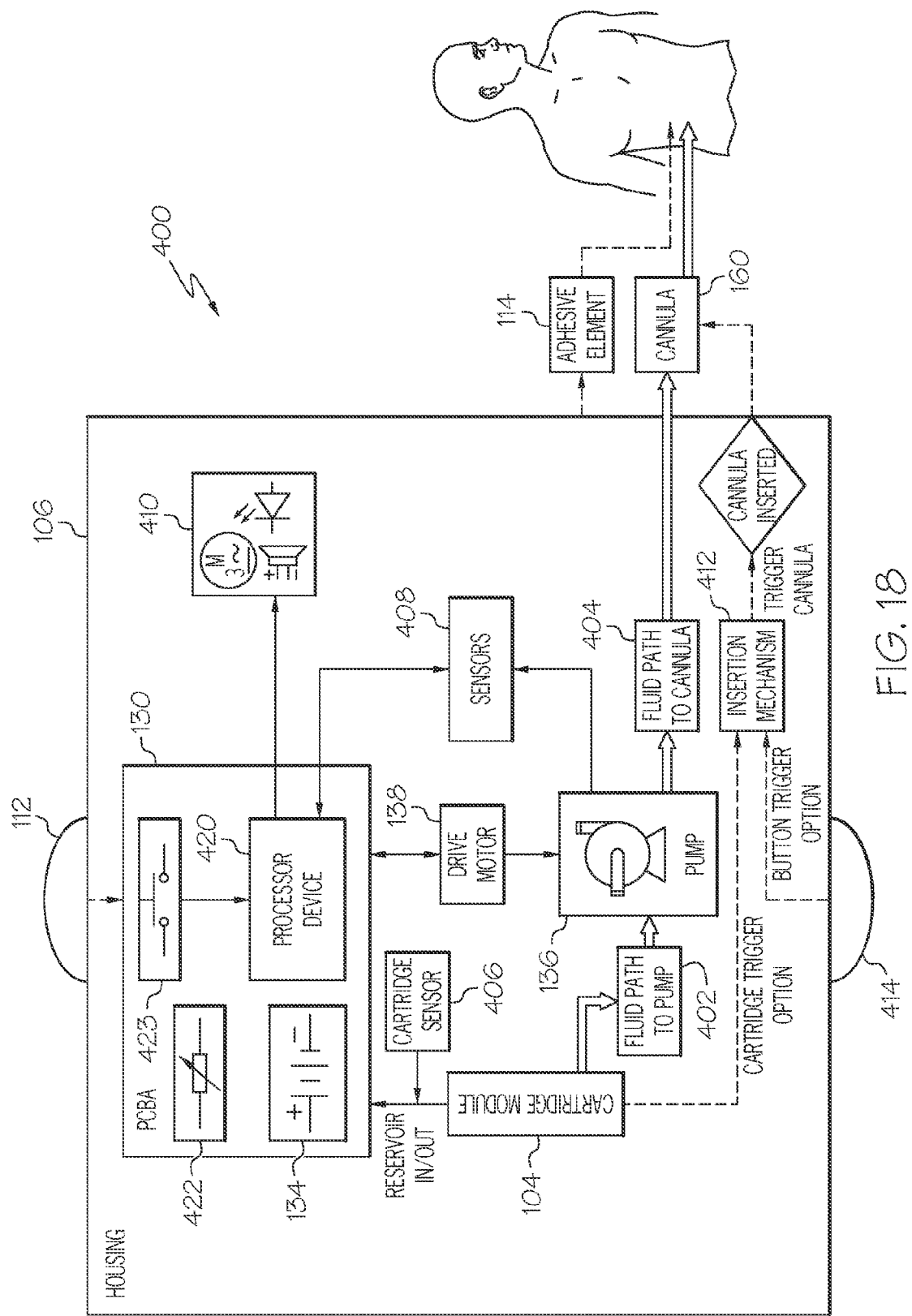

FIG. 11 shows the insertion mechanism 200 in its initial state. If the fluid infusion device 100 has a soft cannula, then the soft cannula is inserted into the body of the patient in the following manner. The first stopper pin 208 is removed to force the first element 202 in the insertion direction (toward the right in FIG. 11). This causes the needle 204 (which carries the soft cannula) to move such that the needle 204 and cannula are inserted into the body, as depicted in FIG. 12 and FIG. 13. The same motion of the first element 202 releases the second stopper pin 214, which in turn releases the spring 212, as depicted in FIG. 14. Releasing the spring 212 moves the second element 210 toward the first element 202, and moves the first element 202 and the needle 204 in the retraction direction. The needle 204 retracts from the body, leaving the soft cannula in place for therapy. If the fluid infusion device 100 includes a rigid cannula, then the first stopper pin 208 is removed to insert the rigid cannula, which remains in place during therapy. At the completion of therapy (or whenever the fluid infusion device 100 is replaced), the second stopper pin 214 is removed to retract the rigid cannula from the body. An exemplary embodiment of an insertion mechanism that employs a living hinge as an actuator arm is described in more detail below with reference to FIGS. 19-24.

In accordance with some embodiments, the conduit insertion mechanism is implemented as a separate component that is external to the fluid infusion device. In this regard, FIGS. 15-17 are perspective views that illustrate the operation of an embodiment of an external insertion mechanism 300. FIG. 15 depicts the insertion mechanism 300 being attached to a fluid infusion device 302 that has already been prepared and affixed to the skin of the patient. In accordance with an alternative design, the insertion mechanism is already attached to the fluid infusion device and the two components are provided as an assembly from the manufacturer (which eliminates the additional step that requires the patient to attach the insertion mechanism). For the illustrated embodiment, a knob 304 of the insertion mechanism 300 is twisted to fire the internal mechanism that inserts the needle/conduit into the body (FIG. 16). Thereafter, the insertion mechanism 300 is removed from the fluid infusion device 302 to retract the insertion needle 306 while leaving the cannula in position (FIG. 17).

FIG. 18 is a block diagram that depicts an exemplary embodiment of a system architecture 400 suitable for use with the fluid infusion device 100. FIG. 18 depicts the housing 106 of the fluid infusion device 100, along with various components, elements, and devices that are housed by, enclosed within, or attached to the housing 106. In FIG. 18, solid arrows represent electrical signal paths, dashed arrows represent mechanical interaction or cooperation between elements, and doubled arrows represent fluid flow paths. It should be appreciated that an embodiment of the system architecture 400 can include additional elements, components, and features that may provide conventional functionality that need not be described herein. Moreover, an embodiment of the system architecture 400 can include alternative elements, components, and features if so desired, as long as the intended and described functionality remains in place.

The illustrated embodiment of the system architecture 400 generally includes, without limitation: the printed circuit board 130; the removable fluid cartridge module 104; the fluid pump mechanism 136; the drive motor 138; a fluid flow path 402; a fluid flow path 404; a cartridge sensor 406; one or more status sensors 408; one or more alerting devices 410; an insertion mechanism 412; and the subcutaneous conduit 160. FIG. 18 includes a number of items that were previously described, and those items will not be redundantly described in detail here.

The printed circuit board 130 may include or carry the electronics of the fluid infusion device 100, e.g., any number of discrete or integrated devices, components, electrical conductors or connectors, and the like. For example, the following items may be found on the printed circuit board 130, without limitation: the battery 134; a processor device 420; a basal rate adjustment component 422; and a switch 423. The printed circuit board 130 (or the items carried by the printed circuit board 130) can be electrically coupled to other elements of the system architecture 400 as needed to support the operation of the fluid infusion device 100. For example, the printed circuit board 130 can be electrically coupled to at least the following, without limitation: the fluid cartridge module 104; the fluid pump mechanism 136; the drive motor 138; the cartridge sensor 406; the status sensors 408; and the alerting devices 410. It should be appreciated that electrical connections to the printed circuit board 130 can be direct or indirect if so desired. Moreover, one or more components on the printed circuit board 130 may support wireless data communication in some embodiments.

The flow path 402 fluidly couples the fluid cartridge module 104 to the inlet of the fluid pump mechanism 136, and the flow path 404 fluidly couples the outlet of the fluid pump mechanism 136 to the subcutaneous conduit 160. The subcutaneous conduit 160 is fluidly coupled to the body of the patient. The drive motor 138 is electrically and mechanically coupled to the fluid pump mechanism 136 to control the operation of the fluid pump mechanism 136. Thus, the drive motor 138 can be turned on and off as needed by the processor device 420 to control the position of the rotor of the fluid pump mechanism 136.

The status sensors 408 can be electrically coupled to the fluid pump mechanism 136 and to the printed circuit board 130 to monitor certain operating conditions, parameters, or characteristics of the fluid pump mechanism 136 and/or other components of the fluid infusion device 100. For example, the information provided by the status sensors 408 can be processed or otherwise utilized to determine the revolution count of the fluid pump mechanism 136, to determine the resting position of the fluid pump mechanism 136, to detect a downstream occlusion in the fluid delivery path, to detect when the reservoir of the fluid cartridge module 104 is empty, or the like.

The alerting devices 410 can be electrically coupled to the printed circuit board 130 for purposes of controlled activation. In this regard, activation of the alerting devices 410 can be controlled by the processor device 420 as needed. In certain embodiments, user manipulation of the button 112 results in actuation of the switch 423, which in turn disables alerts or alarms generated by the alerting devices 410.

The dashed arrow labeled "Cartridge Trigger Option" in FIG. 18 represents mechanical interaction (and/or electrical, magnetic, inductive, optical, capacitive, or other detection methodology) between the fluid cartridge module 104 and the insertion mechanism 412. In this regard, installation of the fluid cartridge module 104 into the housing 106 can be detected to trigger the insertion mechanism 412. If the subcutaneous conduit 160 is not yet inserted in the body of the patient (i.e., the spring mechanism has not been actuated), then the insertion mechanism 412 fires to position the subcutaneous conduit 160 into a subcutaneous location. In alternative embodiments, the insertion button 414 is used to fire the insertion mechanism 412. Accordingly, the dashed arrow labeled "Button Trigger Option" in FIG. 18 represents mechanical interaction (and/or some other detection methodology) between the insertion button 414 and the insertion mechanism 412. In accordance with this option, the insertion mechanism 412 is triggered by physical manipulation of the insertion button 414, and the subcutaneous conduit 160 is installed (unless the insertion mechanism 412 has already been fired).

The processor device 420 can be realized in any form factor. In certain embodiments, the processor device 420 is realized as an application specific integrated circuit (ASIC) that is mounted to the printed circuit board 130. The ASIC can also include a suitable amount of memory that is needed to support the operations and functions of the fluid infusion device. In this regard, techniques, methods, and processes may be described herein in terms of functional and/or logical block components, and with reference to symbolic representations of operations, processing tasks, and functions that may be performed by various computing components or devices. Such operations, tasks, and functions are sometimes referred to as being computer-executed, computerized, software-implemented, or computer-implemented. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

When implemented in software or firmware, various elements of the systems described herein are essentially the code segments or computer-readable instructions that perform the various tasks. In certain embodiments, the program or code segments are stored in a tangible processor-readable medium, which may include any medium that can store or transfer information. Examples of a non-transitory and processor-readable medium include an electronic circuit, a semiconductor memory device, a ROM, a flash memory, an erasable ROM (EROM), a floppy diskette, a CD-ROM, an optical disk, a hard disk, or the like. The software that performs the described functionality may reside and execute at, for example, an ASIC.

More specifically, the processor device 420 may be implemented or performed with a general purpose processor, a content addressable memory, a digital signal processor, an application specific integrated circuit, a field programmable gate array, any suitable programmable logic device, discrete gate or transistor logic, discrete hardware components, or any combination designed to perform the functions described here. In particular, the processor device 420 may be realized as a microprocessor, a controller, a microcontroller, or a state machine. Moreover, the processor device 420 may be implemented as a combination of computing devices, e.g., a combination of a digital signal processor and a microprocessor, a plurality of microprocessors, one or more microprocessors in conjunction with a digital signal processor core, or any other such configuration.

The processor device 420 includes or cooperates with memory, which can be realized as RAM memory, flash memory, EPROM memory, EEPROM memory, registers, or any other form of storage medium known in the art. The memory can be implemented such that the processor device 420 can read information from, and write information to, the memory. In the alternative, the memory may be integral to the processor device 420. As an example, the processor device 420 and the memory may reside in a suitably designed ASIC.

The simple user interface can include a physical button 112, a capacitive button, a thin film force sensitive resistor as a button (using deformation of a specific part of the housing 106 as a button), etc. The button 112 can be activated to deliver a bolus, to remove the device from an inactive shelf mode, to provide a self-check, to respond to alerts or alarms, and the like. The system architecture 400 may include an optional insertion button 414 that can be activated to release the conduit insertion mechanism 412.

One implementation is to have a single software-set basal rate and bolus button value. For example, one SKU can be used for a fluid infusion device having a basal setting of 2 Units/hr, wherein each press of the button 112 results in the delivery of two Units of bolus therapy. A different SKU can be used for a fluid infusion device having a basal setting of 1 U/hr, wherein each press of the button 112 results in the delivery of one Unit of bolus therapy. In practice, the bolus value can be set based on research of total insulin consumption so as to simplify the operation of the device. For example, if a patient uses 100 U/day of basal therapy, they likely need more bolus therapy and, therefore, a 5.0 Unit bolus deliver for each button press might be suitable. On the other hand, if a patient uses 20 U/day of basal therapy, they likely need less bolus therapy and, therefore, the bolus button for the device might be configured to deliver only 1.0 Unit per button press.

Regarding the bolus delivery function, each time the patient presses the button 112, the fluid infusion device 100 delivers the programmed bolus value and waits for the next button press. Thus, if the fluid infusion device 100 has a preset bolus value of 5.0 Units and the patient needs 15.0 Units, then the patient presses the button 112 one time to deliver the first 5.0 Units, presses the button 112 a second time to deliver the next 5.0 Units, and presses the button 112 a third and final time for the last 5.0 Units.

The fluid infusion device 100 also allows for multiple button presses, provides confirmation (vibration, auditory, indicator lights), and then delivers the entire amount. For example, the fluid infusion device 100 may process three back-to-back button presses, recognize a total of three presses, provide user feedback, wait for confirmation, and then deliver a total of 15.0 Units.

The system architecture 400 also supports a feature wherein a physician, caregiver, or the user can adjust the basal rate by supplying an appropriate "key" as described above. The key can have a different form factor or shape for each desired basal rate configuration or setting. When the key is installed in the fluid infusion device 100, it can interact with the printed circuit board 130 via a button, an electrical connection that changes resistance, or the like. In some embodiments, the key can be read using a non-contact methodology such as an RFID chip and related RFID reader. In this way, the key can initiate the changing of certain fluid delivery characteristics, pump settings, etc. The key can be installed on the fluid infusion device 100 or on the fluid cartridge module 104. If the key is installed on the fluid infusion device 100, it can also serve to activate the cannula insertion mechanism 412.

Patient-specific programming can also be achieved through a physician programmer via a wired or wireless communication session. For example, an infrared window can be provided in the housing of the fluid infusion device to accommodate wireless adjustments or programming. Other methods to adjust the basal rate utilize a dial, a knob, or other adjustment component that the physician or patient can manipulate. The adjustment component can be connected to the printed circuit board 130 and, specifically, to the processor device 420 for purposes of changing the timing and/or other characteristics of the fluid pump mechanism 136. FIG. 18 depicts a basal rate adjustment component 422 that is intended to represent the various methodologies and components that serve to adjust the programmed basal rate of the fluid infusion device 100. One simple and low cost way to visualize and confirm the adjustment involves the use of a clear window on the housing of the fluid infusion device and a colored dial with markings corresponding to the adjustment setting.

The system architecture 400 may include or cooperate with any combination of alerting devices 410, including, without limitation: the vibration motor 132 (see FIG. 8 and FIG. 9); a piezoelectric audio transducer; one or more indicator lights (e.g., light emitting diodes or other lamp components); a speaker protected by a hydrophobic membrane; and the like.

The drive motor 138 can be electrically coupled to the printed circuit board 130 with a connector and wires, plated traces on the housing 106, or the like. The drive motor 138 can be coupled to the fluid pump mechanism 136 using a coupler and a spring (not shown). Alternatively, certain embodiments can utilize the one-piece spring coupler 164 described above with reference to FIG. 8 and FIG. 9.

The status sensors 408 can be used to monitor the health and operation of the fluid pump mechanism 136. For example, the status sensors 408 can be used to check the winding resistance of the drive motor 138. The system architecture 400 can also be configured to detect certain fault conditions such as fluid path occlusion, an end of reservoir condition, the Units remaining in the reservoir, and the like. The status sensors 408 can be utilized to check for these and other operating conditions if so desired.

Occlusion can be detected by using a Hall sensor to determine the axial position rate of change of the rotor of the fluid pump mechanism 136. The sensor system can include a magnet positioned on the rotor, and a Hall sensor on the printed circuit board 130. Pumping air rather than fluid, versus not pumping due to an occlusion, will provide a different linear rate of change of the rotor and, therefore, can be correlated to the pumping condition. This methodology will require knowledge of the rotational state of the rotor, i.e., when the rotor has completed one full turn. This can be achieved with a magnetic encoder, an optical encoder, a physical feature on the pump rotor that contacts a switch every time a rotation is complete, or the like. The switch can be a physical, inductive, capacitive, photo-interrupt, or other type of switch. Multiple optical encoders can be used in place of a Hall sensor, one to detect angular position of the rotor, and one to detect linear position. Similarly, magnetic or other encoders can be used.

An end of reservoir condition can be detected using the same methodology described above for occlusion detection, or it can be detected using an optical sensor to monitor the position of the plunger or piston of the fluid cartridge module 104. Other techniques and technologies can also be utilized to determine when the fluid cartridge module 104 needs to be replaced.

The amount of medication fluid remaining can be determined using an optical sensor that detects the location of the plunger near the end of the reservoir volume. A countdown value can be calculated to provide an estimate of the number of Units remaining in the reservoir. Alternatively, the amount of fluid remaining can be determined magnetically by providing a magnet on the plunger of the reservoir. A magnetic sensor in the housing 106 can be used to detect the magnet. As yet another option, inductive or capacitive detection methodologies can be leveraged to determine the amount of medication fluid remaining in the fluid cartridge module 104. The detected position is calibrated to correspond to a specific volume of fluid remaining in the reservoir.

Prefilled fluid cartridge modules 104 can be provided in a housing that facilitates insertion into the housing 106 and removal from the housing 106, as described above. The fluid cartridge modules 104 can be designed to provide a convenient and easy to handle form factor. In certain embodiments, installation of the fluid cartridge module 104 activates the cannula insertion mechanism 412, which eliminates the need for an extra patient step and system component devoted to this function. In FIG. 18, the arrow labeled "Cartridge Trigger Option" represents this functionality.

The fluid cartridge module 104 may be designed with physical features that provide enhanced functionality. For example, physical features of the fluid cartridge module 104 can also be used to distinguish the type or brand of medication fluid contained therein. As another example, a certain feature on the fluid cartridge module 104 may correspond to U100, and the physical feature is configured such that the fluid cartridge module 104 can only be installed in a fluid infusion device that is programmed to deliver at a U100 rate. Likewise, a certain feature on the fluid cartridge module 104 may correspond to U300, and the physical feature is configured such that the fluid cartridge module 104 can only be installed in a fluid infusion device that is programmed to delivery at a U300 rate. In certain embodiments, both can be installed in the same fluid infusion device but with different keying features that activate the appropriate delivery algorithm within the device when installed. This maintains one set of hardware capable of delivering multiple concentrations or medications.

The features on the fluid cartridge module 104 can interact electronically to let the fluid infusion device 100 know what concentration of insulin is in the reservoir by shorting certain contacts, activating specific switches, etc. In this case, the fluid infusion device 100 recognizes the type of fluid cartridge module 104 and takes appropriate action based on the determination made.

The fluid cartridge module 104 may also be configured to communicate to the processor device 420 (or initiate such communication) whether or not it has been installed. The arrow labeled "Reservoir In/Out" in FIG. 18 represents this communication. Thus, the act of inserting the fluid cartridge module 104 into the housing 106 can be electronically detected to take appropriate action. Conversely, if the fluid cartridge module 104 is removed, the fluid infusion device 100 can suspend basal and bolus therapy. When the fluid cartridge module 104 is reinstalled, the therapy can be resumed. The manner in which the fluid cartridge module 104 is detected may vary from one embodiment to another. In certain embodiments, a physical feature on the fluid cartridge module 104 interacts with a feature or a mechanical component of the fluid infusion device 100 that, in turn, triggers a switch on the printed circuit board 130. Alternatively (or additionally), installation of the fluid cartridge module 104 can be achieved by creating a short circuit across electrical contacts when the fluid cartridge module 104 is installed. For example, a metal cap on the fluid cartridge module 104 can serve as the electrical conductor that creates the short circuit. Alternatively, the exterior of the fluid cartridge module 104 can include printed plating or a conductive trace on specific locations that create a short across contacts of the fluid infusion device 100 when the fluid cartridge module 104 is installed. As yet another example, installation of the fluid cartridge module 104 can be detected by physical contact, capacitive sensing, inductive sensing, optical sensing, acoustic sensing, magnetic sensing, infrared sensing, RFID technology, or the like. The cartridge sensor 406 depicted in FIG. 18 is intended to represent these and other possible methodologies, components, and features that detect when the fluid cartridge module 104 is seated/installed, and when the fluid cartridge module 104 is unseated/uninstalled.

Insertion Mechanism with Living Hinge

Figure 19:
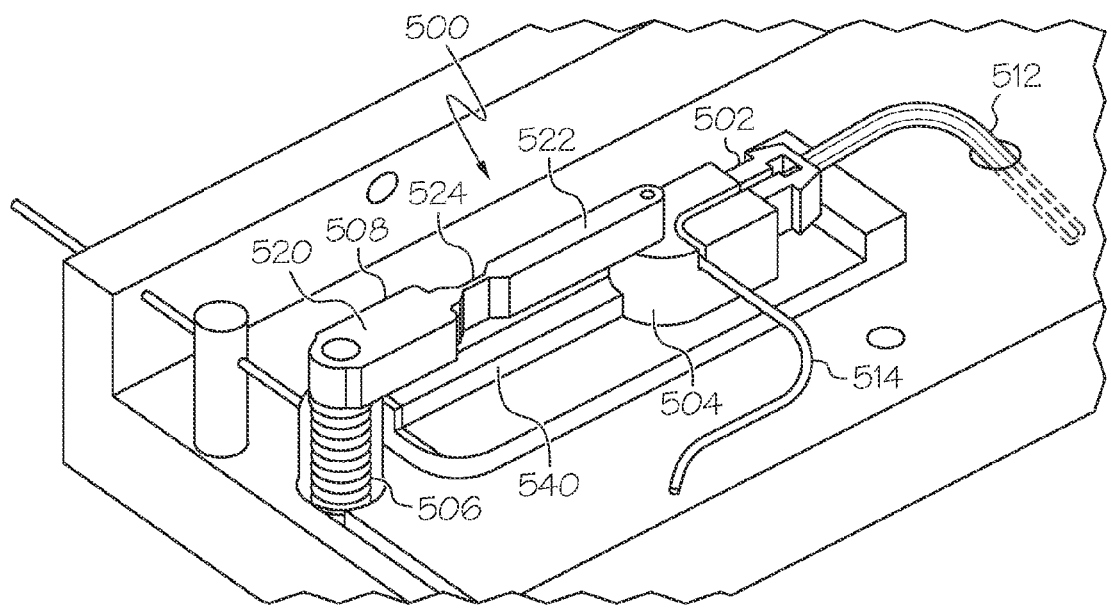
FIG. 19 is a perspective view of an embodiment of a conduit insertion mechanism that utilizes a living hinge.

As described above, the fluid infusion device 100 includes an insertion mechanism for actuating a transcutaneous conduit assembly, wherein actuation of the transcutaneous conduit assembly inserts the subcutaneous conduit 160 into the body of the patient. A schematic mock-up of the insertion mechanism 140 is depicted in FIG. 9 and FIG. 10. An exemplary embodiment of an insertion mechanism 500 is depicted in FIG. 19. The general operating principle and configuration of the insertion mechanism 500 is similar to that disclosed in United States Patent Application Publication number 2014/0142508, the content of which is incorporated by reference herein. The insertion mechanism 500 generally includes, without limitation: a first sliding block 502; a second sliding block 504; a torsion spring 506; and a living hinge 508. The insertion mechanism 500 is suitably configured to cooperate with a transcutaneous conduit assembly having a fluid conduit 512 (e.g., the soft subcutaneous conduit 160 described above) and a needle 514.

Figure 20:
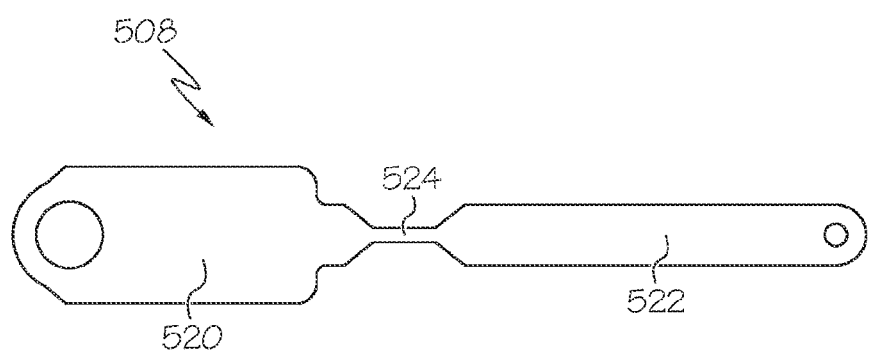
FIG. 20 is a top view of the living hinge shown in FIG. 19.
Figure 21:
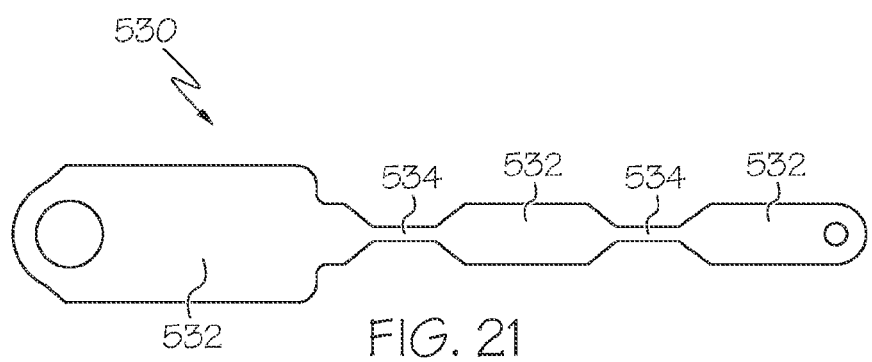
FIG. 21 is a top view of a living hinge having three hinge segments.

FIG. 20 is a top view of the living hinge 508. The illustrated embodiment of the living hinge 508 consists of two and only two segments: a first living hinge segment 520 coupled to the torsion spring 506; and a second living hinge segment 522 coupled to the second sliding block 504. The living hinge 508 also has a flexible junction segment 524 that is integrally formed with the first and second living hinge segments 520, 522. In practice, however, the living hinge of the insertion mechanism 500 can have N living hinge segments integrally formed with N−1 flexible junction segments, where each of the N−1 flexible junction segments serves as a hinge for two adjacent living hinge segments, and where N is an integer greater than one. For example, FIG. 21 is a top view of a living hinge 530 having three living hinge segments 532 and having two flexible junction segments 534.

Referring again to FIG. 19 and FIG. 20, the flexible junction segment 524 is thin enough to function as a hinge, yet strong enough to remain intact during manufacturing, assembly, and storage of the fluid infusion device 100. Of course, the flexible junction segment 524 must also be strong enough to handle the mechanical forces necessary to move the second sliding block 504 to insert the conduit during the insertion action. Moreover, the flexible junction segment 524 is strong enough to withstand the torsional forces imparted by the torsion spring 506 during activation of the insertion mechanism 500.

The living hinge 508 can be fabricated as a one-piece component. For example, the living hinge 508 can be formed from a molded material such as an injection molded plastic, nylon, or the like. For the illustrated embodiment, the living hinge 508 is a physically distinct component that is mechanically coupled between the torsion spring 506 and the second sliding block 504. Alternatively, the living hinge 508 and the second sliding block 504 can be integrally formed as a one-piece component. Thus, the living hinge 508 and the second sliding block 504 can be molded together from the same material. In other embodiments, the living hinge 508 and the torsion spring 506 can be integrally formed as a one-piece component. For example, the living hinge 508 and the torsion spring 506 can be molded together from the same material. In yet other embodiments, the torsion spring 506, the living hinge 508, and the second sliding block 504 can be integrally formed as a one-piece component if so desired.

Figure 24:
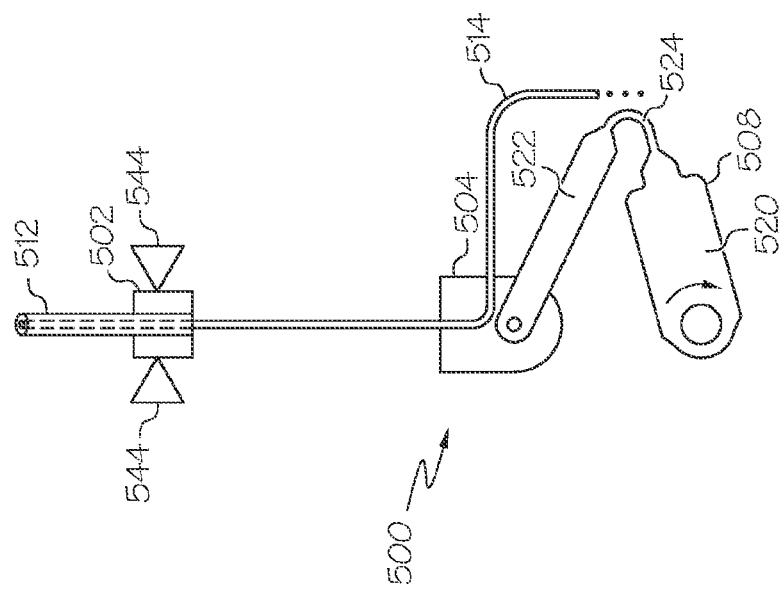
FIGS. 22-24 are schematic top views that illustrate actuation of a conduit insertion mechanism.
Figure 23:
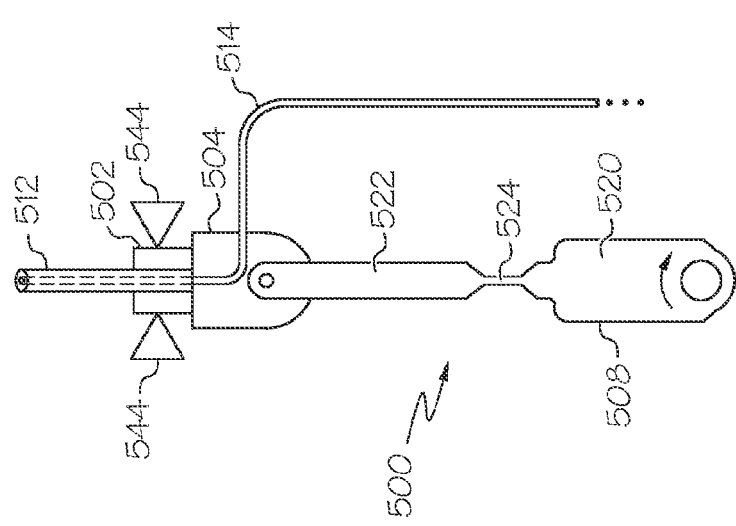
Figure 22:
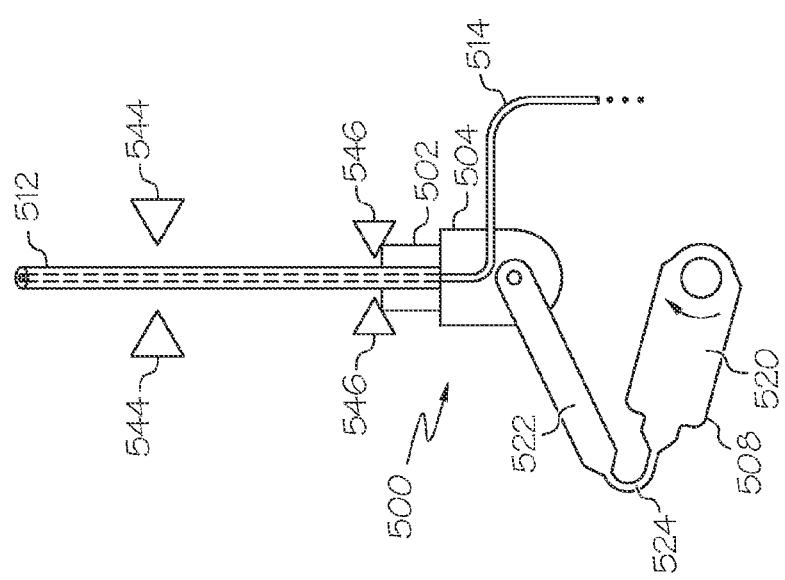

The insertion mechanism 500 relies on the living hinge segments (arms), which have one rotational degree of freedom about each other. The torsion spring 506 is anchored to the first living hinge segment 520 to generate rotational movement of the first living hinge segment 520 when the torsion spring 506 is released or activated. The second living hinge segment 522 is attached to the second sliding block 504, which is constrained on a linear track 540 or equivalent structure that guides the second sliding block 504 in an insertion direction and in a retraction direction (opposite the insertion direction). With reference to FIGS. 22-24 (which are schematic top views that illustrate actuation of the insertion mechanism 500), the insertion direction corresponds to upward movement of the first and second sliding blocks 502, 504, and the retraction direction corresponds to downward movement of the second sliding block 504.

Accordingly, rotation of the torsion spring 506 during an insertion action actuates the living hinge 508 to move the second sliding block 504 in the insertion direction, which in turn results in forward movement of the first sliding block 502 in the insertion direction (see FIG. 23). For this particular example, rotation of the torsion spring 506 in the clockwise direction depicted in FIGS. 22-24 corresponds to the activation and firing of the insertion mechanism 500. Thus, continued rotation of the first living hinge segment 520 in the clockwise direction causes the second sliding block 504 to be pulled back in the retraction direction (see FIG. 24). In other words, the net movement of the insertion mechanism 500 corresponds to a forward movement of the first and second sliding blocks 502, 504 during the first half of rotation, and a backward movement of the second sliding block 504 during the second half of rotation.

The insertion mechanism 500 can include or cooperate with a suitably configured lock mechanism 544 (which is schematically depicted in FIGS. 22-24). The lock mechanism 544 is designed to maintain the first sliding block 502 in its upward deployed position, while allowing the second sliding block 504 to return to its initial position (see FIG. 24). The lock mechanism 544 can be realized as a latch, retaining clips, or any suitably configured structure that secures and holds the first sliding block 502 in place after the living hinge 508 and the second sliding block 504 urge the first sliding block 502 to engage the lock mechanism 544.

The insertion mechanism 500 can also include a triggering lock mechanism 546 (which is schematically depicted in FIG. 22). The triggering lock mechanism 546 is suitably configured to maintain the first sliding block 502 and the second sliding block 504 in an initial position, as shown in FIG. 22. The triggering lock mechanism 546 is also designed to maintain the torsion spring 506 in a loaded state. The triggering lock mechanism 546 is released to activate the insertion mechanism 500 as needed. The triggering lock mechanism 546 can be released in response to manipulation of the button 112 or the insertion button 414 (see FIG. 18). In some implementations of the fluid infusion device 100, the triggering lock mechanism 546 is automatically released to activate the insertion mechanism 500 in response to installation of the removable fluid cartridge module 104 in the housing 106.

The first sliding block 502 is coupled to the fluid conduit 512 such that the fluid conduit 512 can move in concert with the first sliding block 502. In certain embodiments, the proximal end of the fluid conduit 512 terminates at or within the first sliding block 502. Thus, the first sliding block 502 moves the fluid conduit 512 in the insertion direction when the insertion mechanism is activated. The fluid conduit 512 is "carried" by the needle 514 during the insertion operation. In this regard, at least a portion of the needle 514 is initially inside the fluid conduit 512. The second sliding block 504 is coupled to the needle 514 to move the distal end of the needle 514 in the insertion direction and in a retraction direction. For the illustrated embodiment, the needle 514 is secured to the second sliding block 504 such that the needle 514 moves in concert with the second sliding block 504. The needle 514 corresponds to the outlet fluid conduit 142 shown in FIGS. 8-10. In other words, the needle 514 is a hollow conduit that functions to insert the fluid conduit 512 and, thereafter, to deliver the medication fluid to the fluid conduit 512. As depicted in FIGS. 22-24, the insertion mechanism 500 achieves the insertion and retraction of the needle 514 in only one rotational motion.

The use of a single injection molded living hinge 508 allows for a reduction of parts, a reduction in manufacturing processes, and improved reliability and more consistent performance relative to a conventional design that utilizes physically distinct hinge components. Moreover, if the second sliding block 504 and/or the torsion spring 506 are integrally molded with the living hinge 508, then a further reduction in parts count and complexity is achieved.

In accordance with an alternative embodiment, the living hinge 508 can be fabricated from a single piece of metal having the ductility that is desired to create the flexible junction segment (or segments). A metal-based living hinge 508 can be desirable to address potential issues related to stress relaxation of polymeric-based living hinges held under the torsion spring load (i.e., when the torsion spring 506 is held in compression against the living hinge 508 in the shipping and storage state of the fluid infusion device).

It should be appreciated that the insertion mechanism 500 can be designed to separate the insertion procedure from the retraction procedure. This methodology can be used in an embodiment of the fluid infusion device 100 that includes a steel cannula, wherein retraction of the steel cannula occurs after completion of therapy (e.g., when the fluid infusion device 100 is replaced).

Triggering Functions Based on Fluid Cartridge Installation

Figure 25:
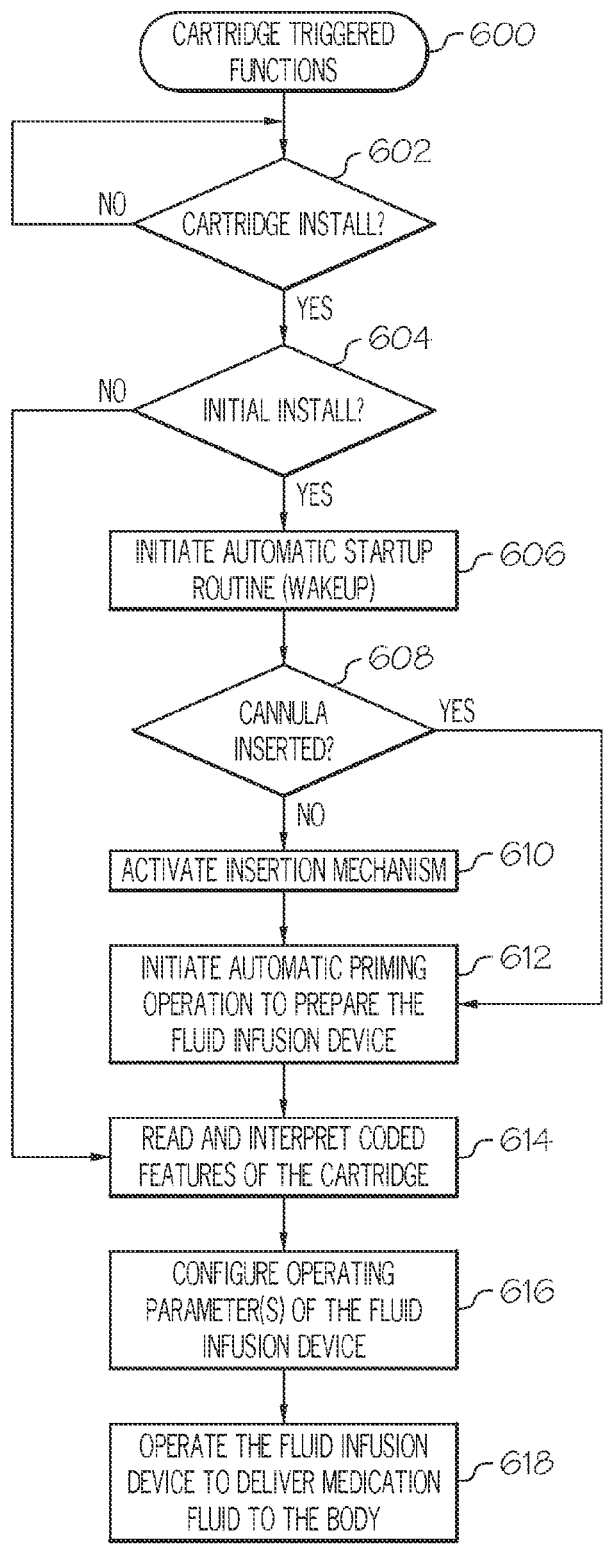
FIG. 25 is a flow chart that illustrates an embodiment of a process for performing various cartridge-triggered functions.

The fluid infusion device 100 described herein is designed to be simple and easy to use. To this end, the fluid infusion device 100 can be configured to support various "automatic" functions that are performed when the fluid infusion device 100 is initially deployed. In particular, a number of functions, routines, or operations can be triggered in response to the installation of the fluid cartridge module 104 into the housing 106. In this regard, FIG. 25 is a flow chart that illustrates an embodiment of a process 600 for performing various cartridge-triggered functions. The various tasks performed in connection with a process described herein may be performed by software, hardware, firmware, or any combination thereof. In certain embodiments of the fluid infusion device, the processor device 420 (FIG. 18) executes computer readable program instructions to perform at least some of the tasks associated with the process 600.

For illustrative purposes, the description of an illustrated process may refer to elements mentioned above in connection with FIGS. 1-24. In practice, portions of a described process may be performed by different elements of the described system, e.g., a processor device, an electronic component, a mechanical component, or the like. It should be appreciated that a process described herein may include any number of additional or alternative tasks, the tasks shown in the figures need not be performed in the illustrated order, and a process described herein may be incorporated into a more comprehensive procedure or process having additional functionality not described in detail herein. Moreover, one or more of the tasks shown in a figure could be omitted from an embodiment of the illustrated process as long as the intended overall functionality remains intact.

The following description of the process 600 assumes that the housing 106 of the fluid infusion device 100 has already been affixed to the body of the patient. The process 600 may begin when installation of a removable fluid cartridge module is detected (the "Yes" branch of query task 602). The process 600 can detect the presence or installation of the fluid cartridge module using any number of detection schemes or methodologies. For example, the fluid cartridge module may have a structural feature that cooperates with an associated structural feature of the fluid infusion device 100, such that the structural features interact with (or engage) each other when the fluid cartridge module is properly installed. As another example, the fluid cartridge module may include or carry an electrically conductive element that cooperates with an electronic detection circuit on the printed circuit board 130. The conductive element on the fluid cartridge module contacts the electronic detection circuit when the fluid cartridge module is properly installed in the fluid infusion device 100. As yet another example, the cartridge sensor 406 (FIG. 18) or another sensor system can be used to detect when the fluid cartridge module is installed in the housing 106. These and other detection methodologies are contemplated by this disclosure.

In practice, the fluid infusion device 100 can be realized as a multiple-day disposable device that can accommodate the removal and replacement of any number of fluid cartridge modules. Accordingly, the process 600 may check whether the fluid cartridge module is the first or initial cartridge module (the "Yes" branch of query task 604) or a replacement cartridge module (the "No" branch of query task 604). As mentioned above, this description assumes that the fluid infusion device is newly deployed and, therefore, that the fluid cartridge module is the initial installation. It should be appreciated that the "No" branch of query task 604 is followed for each fluid cartridge module that is installed after the first cartridge module has been removed. The electronics of the fluid infusion device 100 can maintain a cartridge status or count that indicates the number of times a fluid cartridge module has been installed, and query task 604 can poll the count as needed.

In response to the installation of the first fluid cartridge module, the process 600 initiates an automatic startup routine (task 606). The automatic startup routine is performed to wake up the electronics of the fluid infusion device 100 (if needed) and to transition the fluid infusion device 100 from a "dormant" shipping and storage condition to an active or standby condition. The process 600 checks whether the cannula is already inserted (query task 608). Query task 608 may serve as a safety measure, or as a check to ensure that the insertion mechanism has not been inadvertently fired. Under normal circumstances, the cannula will not be inserted until the insertion mechanism is properly activated. Nonetheless, the process 600 contemplates a scenario where the cannula is already inserted (the "Yes" branch of query task 608). If so, then the process 600 may exit or proceed to a task 612, which is described in more detail below.

This example assumes that the cannula has not yet been inserted into the body of the patient (the "No" branch of query task 608). Accordingly, the process 600 automatically activates the insertion mechanism (task 610) to insert the fluid conduit or cannula into the body. Notably, under expected and typical operating conditions, task 610 is automatically initiated when the fluid cartridge module is initially installed in the housing. Task 610 may be associated with a purely mechanical actuation (e.g., the fluid cartridge module physically engages a switch, a pin, or a latch mechanism to fire the insertion mechanism), an electrical trigger (e.g., the presence of the fluid cartridge module is detected), which in turn causes the insertion mechanism to be electronically triggered, or a combination thereof. In certain embodiments, installation of the fluid cartridge module releases the triggering lock mechanism 546 that maintains the insertion mechanism 500 in its initial loaded state (see FIG. 22).

The insertion mechanism operates in the manner described above to insert the fluid conduit into the body of the patient. After the insertion mechanism inserts the fluid conduit into the body, the process 600 continues by initiating an automatic priming operation to prepare the fluid infusion device for delivery of the medication fluid (task 612). Task 612 is associated with the controlled and calibrated operation of the fluid pump mechanism to expel air from the fluid flow path of the fluid infusion device 100 and to prime the fluid infusion device 100 with medication fluid obtained from the fluid cartridge module. More specifically, the automatic priming operation primes the fluid flow path 402, the fluid pump mechanism 136, and the fluid flow path 404, which may include the fluid conduit or subcutaneous conduit 160 (FIG. 18), with the medication fluid to prepare the fluid infusion device 100 for delivery of the medication fluid. In practice, the automatic priming operation controls the activation of the drive motor 138 to actuate the fluid pump mechanism 136 by a predetermined amount, e.g., to perform a designated number of rotations, resulting in a corresponding number of pump cycles. In this regard, the predetermined amount can be calibrated in accordance with a combined fluid volume of the fluid flow path 402, the fluid pump mechanism 136, and the fluid flow path 404. The automatic priming operation can be calibrated based on the known, designed, and/or empirically determined volume of the flow path, the specifications of the fluid pump mechanism 136, and the like. Once calibrated, the appropriate control instructions can be programmed into the electronics of the fluid infusion device 100 for execution during task 612. In some embodiments, the priming can be performed with calibrated readings from one or more sensors of the fluid infusion device, such as pressure sensors, Hall sensors, or the like).

The illustrated embodiment of the process 600 also contemplates the use of coded features associated with the fluid cartridge module. The coded features can be integrated into the fluid cartridge module, carried by the fluid cartridge module, printed on the fluid cartridge module, or the like. As described above, for example, the coded features can be realized as a physical key or any detectable key feature. As another example, the coded features can be realized as an optically readable pattern, design, or layout, such as a bar code. Similarly, the coded features can be realized as electrically, optically, or magnetically detectable features of the fluid cartridge module. As yet another example, the coded features can be realized as physical characteristics (tabs, bumps, slots, or other detectable features) of the fluid cartridge module. These and other coding techniques and methodologies are contemplated by this disclosure.

In response to the installation of the fluid cartridge module, the process 600 reads and interprets the coded features (task 614). Task 614 may involve, for example, the cartridge sensor 406, the status sensors 408, or the like. The coded features are read and analyzed for purposes of making adjustments, changing configuration settings, or the like. For example, the process 600 can configure at least one operating parameter of the fluid infusion device in accordance with the coded features as interpreted (task 616). In accordance with certain embodiments, task 616 adjusts or otherwise sets the basal rate of the medication fluid to be delivered by the fluid infusion device. As another example, the coded features can be indicative of at least one characteristic of the medication fluid contained in the fluid cartridge module. Thus, the coded features may identify the type of medication fluid, the concentration, or the like, wherein task 616 can adjust certain operating parameters based on the characteristics of the medication fluid.

After task 616 adjusts and configures the fluid infusion device, the process 600 continues by operating the fluid infusion device to deliver the medication fluid to the body of the patient (task 618). As explained above, the bulk of the process 600 is performed once for each deployment of a new fluid infusion device. The removable fluid cartridge module can be replaced as needed, using the same fluid infusion device. In a typical scenario, one fluid infusion device can be worn by the patient for several days while accommodating multiple replacement cartridge modules, e.g., one or two cartridge modules per day. Thus, the startup routine, the insertion operation, and the priming operation are usually not repeated for fluid cartridge modules that are installed after the first fluid cartridge module is removed.

Hot Swappable Fluid Cartridge Module

As mentioned above, certain embodiments of the fluid infusion device 100 are provided as disposable products, wherein one instantiation of the fluid infusion device 100 is worn for a limited period of time before it is replaced with a new instantiation. For example, the fluid infusion device 100 can be designed for single-day use, for use over a few days, for use during one week, or the like. Due to the compact size of the fluid infusion device 100, it may be necessary to replace the removable fluid cartridge module 104 one or more times during the course of therapy. Thus, multiple fluid cartridge modules 104 can be used without having to remove the fluid infusion device 100 from the body of the patient.

The fluid infusion device 100 is suitably configured to accommodate "hot swapping" of removable fluid cartridge modules 104, regardless of the amount of medication fluid that may remain. Hot swapping allows the fluid infusion device 100 to remain in a suspended state during periods of time when no fluid cartridge module 104 is present. After detecting the installation of a replacement fluid cartridge module 104, the fluid infusion device 100 automatically transitions back to the normal operating mode without having to carry out a fluid priming operation and without having to make further adjustments or configuration changes.

Figure 26:
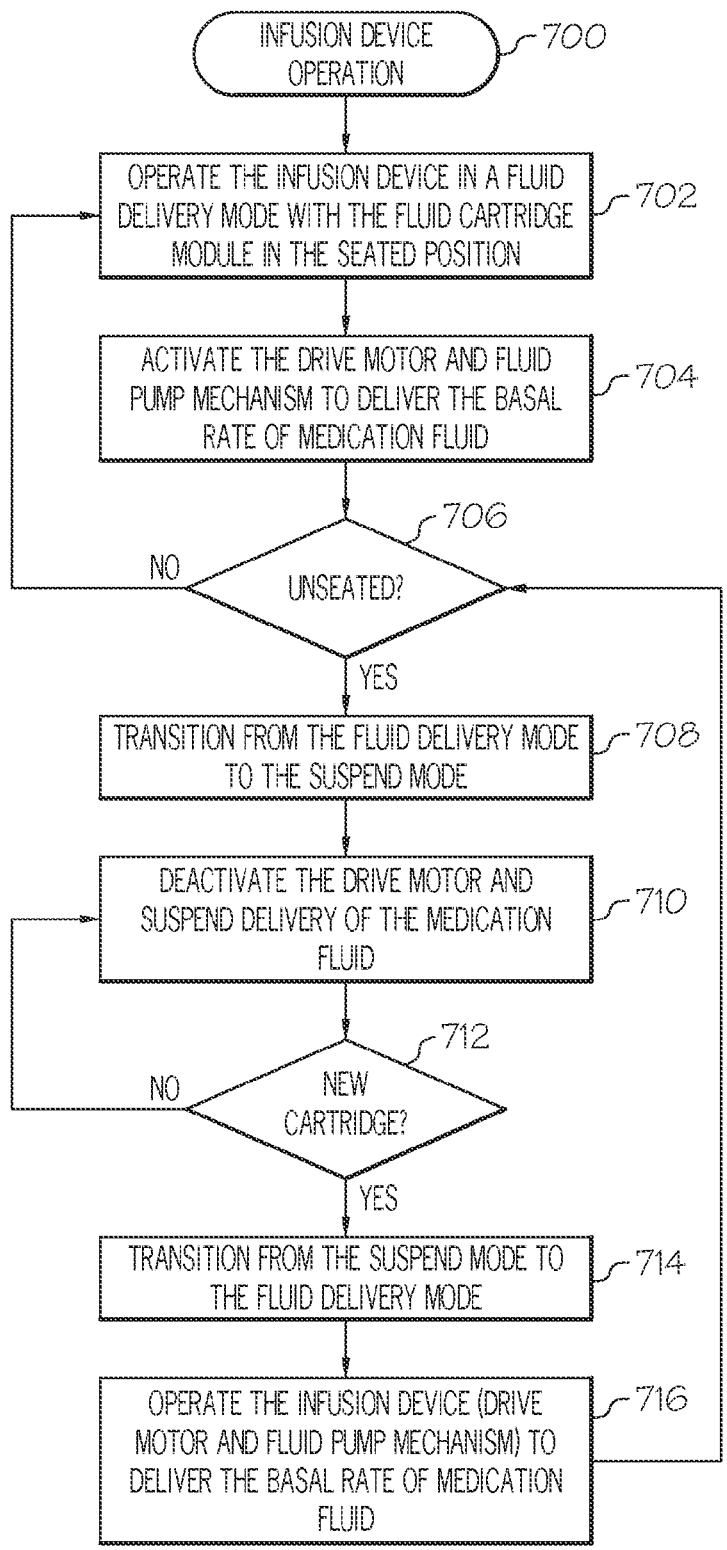
FIG. 26 is a flow chart that illustrates an embodiment of a process for operating a fluid infusion device.

FIG. 26 is a flow chart that illustrates an embodiment of a process 700 for operating a fluid infusion device. In certain embodiments of the fluid infusion device 100, the processor device 420 (FIG. 18) executes computer readable program instructions to perform at least some of the tasks associated with the process 700. This description assumes that the fluid infusion device 100 is already operating in a fluid delivery mode (task 702). The fluid delivery mode can be considered to be the typical or normal operating mode, which is supported when the removable fluid cartridge module 104 is properly installed in a seated position within the housing 106 of the fluid infusion device 100. The process 700 may leverage any of the cartridge detection techniques and methodologies described above to confirm whether or not the fluid cartridge module 104 is properly seated (see, for example, the description associated with task 602 of the process 600). While operating during the fluid delivery mode, the process 700 controls the activation of the drive motor 138 to cause the fluid pump mechanism 136 to deliver a predetermined or preset basal rate of the medication fluid (task 704). Task 704 may be associated with actuation of the fluid pump mechanism 136 according to a controlled schedule to pump the medication fluid from the fluid cartridge module 104 to the body of the patient, via a subcutaneous conduit 160 (e.g., a cannula). Although not separately depicted in FIG. 26, the fluid infusion device 100 also supports the delivery of patient-administered boluses while operating in the fluid delivery mode.

The process 700 monitors the state of the removable fluid cartridge module 104 to detect the occurrence of a cartridge removal event that is indicative of a transition of the removable fluid cartridge module 104 from the normal seated position to an unseated position (query task 706). As mentioned above, the process 700 can leverage any of the previously described cartridge detection or sensing technologies to determine whether the fluid cartridge module 104 becomes unseated. For example, the detectable cartridge removal event may be associated with releasing of the retention mechanism 110 of the fluid cartridge module 104 (see FIGS. 1 and 3-5). As another example, the cartridge removal event may be associated with physical interaction between structural features of the fluid cartridge module 104 and the housing 106, or between the fluid cartridge module 104 and other components of the fluid infusion device 100. Other non-limiting techniques involve electrical, magnetic, inductive, optical, capacitive, RFID based, or resistive sensing technologies.

This example assumes that the process 700 detects a transition of the fluid cartridge module 104 from the seated position to an unseated position (the "Yes" branch of query task 706). In response to the detecting, the process 700 reconfigures and operates the fluid infusion device 100 to transition from the fluid delivery mode to the suspend mode (task 708). In this regard, the process 700 deactivates the drive motor 138, which in turn disables the fluid pump mechanism 136 to suspend delivery of the medication fluid to the body (task 710). Deactivating the fluid pump mechanism 136 in this manner preserves the primed state of the fluid flow path of the fluid infusion device 100. Moreover, as described above with reference to FIG. 9, in the absence of a fluid cartridge module, the sealing element 154 forms a fluid seal to inhibit leakage of the medication fluid from the end of the hollow reservoir needle 152. This example assumes that the fluid infusion device 100 need not be replaced at this time. Accordingly, the housing 106 remains affixed to the body during the suspend mode, and the distal end of the subcutaneous conduit remains subcutaneously positioned within the body during the suspend mode. In other words, the fluid infusion device 100 remains as-is to accommodate removal and replacement of fluid cartridge modules 104.

The fluid infusion device 100 can remain in the suspend state for any reasonable period of time. If, for example, the patient is quickly installing a new fluid cartridge module 104, then the suspend period will be relatively short. In certain situations, however, a replacement fluid cartridge module 104 may not be installed for a few hours. In either scenario, the process 700 can keep the fluid infusion device 100 in the suspend mode. If a replacement cartridge module 104 is not inserted after a threshold period of time has lapsed, then an alert or notification can be generated to remind the user.

This example assumes that a new or replacement fluid cartridge module 104 is eventually installed (the "Yes" branch of query task 712). In this regard, the process 700 can detect or otherwise determine the occurrence of a cartridge insertion event that is indicative of positioning of a replacement removable cartridge module 104 into the seated position. Again, the fluid infusion device 100 can leverage any of the cartridge detection or sensing techniques and methodologies mentioned above. In response to the installation of a replacement cartridge module 104, the process 700 transitions the fluid infusion device 100 from the suspend mode and back to the fluid delivery mode (task 714). This transition causes the drive motor 138 and the fluid pump mechanism 136 to resume normal operation to deliver the designated basal rate of the medication fluid to the body (task 716).

FIG. 26 depicts task 716 leading back to query task 706. This allows the process 700 to continue monitoring the status of the fluid cartridge module 104 in the manner described above. In practice, therefore, the fluid infusion device 100 can be switched between the fluid delivery mode and the suspend mode any number of times before it needs to be discarded.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A fluid infusion device for delivering a medication fluid to a body, the fluid infusion device comprising:
   a housing that receives a fluid cartridge module comprising an electrically conductive element;
   an electronic detection circuit having electrically conductive terminals;
   a fluid pump mechanism within the housing;
   a drive motor coupled to actuate the fluid pump mechanism;
   a transcutaneous conduit assembly comprising a fluid conduit in fluid communication with the fluid pump mechanism;
   an insertion mechanism for inserting the fluid conduit into the body; and
   a processor device operatively coupled to the drive motor, wherein the processor device executes computer readable program instructions to initiate an automatic startup routine when the fluid cartridge module is initially installed in the housing, in response to contact between the electrically conductive element of the fluid cartridge module and the electrically conductive terminals of the electronic detection circuit;
   wherein the insertion mechanism is automatically activated to insert the fluid conduit into the body when the fluid cartridge module is initially installed in the housing.

2. The fluid infusion device of claim 1, wherein:
   the fluid cartridge module comprises coded features; and
   the program instructions executed by the processor device interpret the coded features and automatically configure at least one operating parameter of the fluid infusion device in accordance with the coded features as interpreted.

3. The fluid infusion device of claim 2, wherein the at least one operating parameter comprises a basal rate of the medication fluid to be delivered by the fluid infusion device.

4. The fluid infusion device of claim 2, wherein the coded features are indicative of at least one characteristic of medication fluid contained in the fluid cartridge module.

5. The fluid infusion device of claim 2, wherein the coded features are physical features of the fluid cartridge module.

6. The fluid infusion device of claim 2, wherein the coded features are electrically, optically, or magnetically detectable features of the fluid cartridge module.

7. The fluid infusion device of claim 1, wherein the program instructions executed by the processor device initiate an automatic priming operation when the fluid cartridge module is initially installed in the housing.

8. The fluid infusion device of claim 1, wherein:
the fluid infusion device is a disposable insulin pump device; and
the medication fluid comprises insulin.

9. A method of operating a fluid infusion device comprising a housing, an electronic detection circuit having electrically conductive terminals, a fluid pump mechanism, a transcutaneous conduit assembly having a fluid conduit in fluid communication with the fluid pump mechanism, and an insertion mechanism for inserting the fluid conduit into the body, the method comprising:
detecting a first installation of a fluid cartridge module in the housing, the fluid cartridge module comprising an electrically conductive element, wherein the detecting occurs after the housing has been affixed to the body and in response to contact between the electrically conductive element of the fluid cartridge module and the electrically conductive terminals of the electronic detection circuit; and
in response to the detecting, automatically activating the insertion mechanism to insert the fluid conduit into the body.

10. The method of claim 9, further comprising:
in response to the detecting, initiating an automatic startup routine for the fluid infusion device.

11. The method of claim 9, wherein:
the fluid cartridge module comprises coded features; and
the method further comprises reading the coded features and automatically configuring at least one operating parameter of the fluid infusion device in accordance with the coded features as read.

12. The method of claim 11, wherein the at least one operating parameter comprises a basal rate of the medication fluid to be delivered by the fluid infusion device.

13. The method of claim 11, wherein the coded features are indicative of at least one characteristic of medication fluid contained in the fluid cartridge module.

14. The method of claim 9, further comprising:
after inserting the fluid conduit into the body, initiating an automatic priming operation to prepare the fluid infusion device for delivery of the medication fluid.

15. A fluid infusion device for delivering a medication fluid to a body, the fluid infusion device comprising:
a housing that receives a fluid cartridge module comprising an electrically conductive element;
an electronic detection circuit having electrically conductive terminals;
a fluid pump mechanism within the housing;
a transcutaneous conduit assembly comprising a fluid conduit in fluid communication with the fluid pump mechanism; and
an insertion mechanism for inserting the fluid conduit into the body, the insertion mechanism being automatically activated to insert the fluid conduit into the body when the fluid cartridge module is initially installed in the housing, in response to contact between the electrically conductive element of the fluid cartridge module and the electrically conductive terminals of the electronic detection circuit;
wherein, after the insertion mechanism inserts the fluid conduit into the body, the fluid pump mechanism performs an automatic priming operation to prepare the fluid infusion device for delivery of the medication fluid.

16. The fluid infusion device of claim 15, wherein:
the fluid cartridge module comprises coded features;
the fluid infusion device reads the coded features in response to installation of the fluid cartridge module in the housing; and
at least one operating parameter of the fluid infusion device is automatically configured in accordance with the coded features as read.

17. The fluid infusion device of claim 15, wherein:
the fluid cartridge module comprises coded features;
the fluid infusion device reads the coded features in response to installation of the fluid cartridge module in the housing; and
the coded features are indicative of at least one characteristic of medication fluid contained in the fluid cartridge module.

* * * * *